(12) United States Patent
Cooper et al.

(10) Patent No.: US 10,881,512 B2
(45) Date of Patent: Jan. 5, 2021

(54) DUAL-FLANGE PROSTHETIC VALVE FRAME

(71) Applicant: Edwards Lifesciences Corporation, Irvine, CA (US)

(72) Inventors: Alexander H. Cooper, Costa Mesa, CA (US); Matthew A. Peterson, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 81 days.

(21) Appl. No.: 16/104,015

(22) Filed: Aug. 16, 2018

(65) Prior Publication Data

US 2018/0353295 A1 Dec. 13, 2018

Related U.S. Application Data

(63) Continuation of application No. 14/830,347, filed on Aug. 19, 2015, now Pat. No. 10,058,424.
(Continued)

(51) Int. Cl.
*A61F 2/24* (2006.01)
*A61F 2/966* (2013.01)

(52) U.S. Cl.
CPC .............. *A61F 2/2436* (2013.01); *A61F 2/24* (2013.01); *A61F 2/2418* (2013.01);
(Continued)

(58) Field of Classification Search
CPC ........ A61F 2/24; A61F 2/2412; A61F 2/2418; A61F 2/2436
See application file for complete search history.

(56) References Cited

U.S. PATENT DOCUMENTS 3,409,013 A 11/1968 Berry
3,472,230 A 10/1969 Fogarty
(Continued)

FOREIGN PATENT DOCUMENTS

DE 2246526 A1 3/1973
DE 19532846 A1 3/1997
(Continued)

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.
(Continued)

*Primary Examiner* — Dinah Baria
(74) *Attorney, Agent, or Firm* — Klarquist Sparkman LLP

(57) ABSTRACT

A method of replacing the function of a native mitral valve is achieved by inserting a distal end portion of a delivery apparatus into a patient's body, wherein a prosthetic mitral valve is disposed along the distal end portion of the delivery apparatus. The prosthetic mitral valve includes a collapsible and expandable annular body having a network of struts interconnected at a plurality of nodes to form a plurality of open cells. Atrial and ventricular flanges are coupled to the annular body and extend radially away from the annular body. Three commissure support posts extend from the ventricular flange toward a ventricular end of the prosthetic valve and a valve member is secured to the commissure support posts. The prosthetic mitral valve is positioned within the native mitral valve of the patient's heart and the native mitral valve is pinched between the atrial and ventricular flanges.

19 Claims, 13 Drawing Sheets

Related U.S. Application Data

(60) Provisional application No. 62/040,099, filed on Aug. 21, 2014.

(52) U.S. Cl.
CPC ..... *A61F 2/2412* (2013.01); *A61F 2002/9665* (2013.01); *A61F 2220/0008* (2013.01); *A61F 2230/005* (2013.01); *A61F 2230/0052* (2013.01); *A61F 2230/0067* (2013.01); *A61F 2230/0069* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,287,339 B1 | 9/2001 | Vazquez et al. |
| 6,299,637 B1 | 10/2001 | Shaolian et al. |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely |
| 6,575,959 B1 | 6/2003 | Sarge et al. |
| 6,582,462 B1 | 6/2003 | Andersen et al. |
| 6,605,112 B1 | 8/2003 | Moll et al. |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |

(56) References Cited

U.S. PATENT DOCUMENTS

| | | |
|---|---|---|
| 7,276,084 B2 | 10/2007 | Yang et al. |
| 7,318,278 B2 | 1/2008 | Zhang et al. |
| 7,338,520 B2 | 3/2008 | Bailey et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,524,330 B2 | 4/2009 | Berreklouw |
| 7,530,253 B2 | 5/2009 | Spenser et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,892,281 B2 | 2/2011 | Seguin et al. |
| 7,914,575 B2 | 3/2011 | Guyenot et al. |
| 7,993,394 B2 | 8/2011 | Hariton et al. |
| 8,007,992 B2 | 8/2011 | Tian et al. |
| 8,029,556 B2 | 10/2011 | Rowe |
| 8,092,521 B2 | 1/2012 | Figulla et al. |
| 8,118,866 B2 | 2/2012 | Herrmann et al. |
| 8,167,932 B2 | 5/2012 | Bourang |
| 8,206,437 B2 | 6/2012 | Bonhoeffer et al. |
| 8,216,174 B2 | 7/2012 | Wilk et al. |
| 8,317,858 B2 | 11/2012 | Straubinger et al. |
| 8,398,704 B2 | 3/2013 | Straubinger et al. |
| 8,416,643 B2 | 4/2013 | Magee |
| 8,449,599 B2 | 5/2013 | Chau et al. |
| 8,460,370 B2 | 6/2013 | Zakay |
| 8,579,964 B2 | 11/2013 | Lane et al. |
| 9,173,737 B2 | 11/2015 | Hill et al. |
| 9,393,111 B2 | 7/2016 | Ma et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0023300 A1 | 1/2003 | Bailey et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0092858 A1 | 5/2004 | Wilson et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0137688 A1 | 6/2005 | Salahieh et al. |
| 2005/0137698 A1 | 6/2005 | Salahieh et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0025857 A1 | 2/2006 | Bergheim et al. |
| 2006/0058872 A1 | 3/2006 | Salahieh et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0195134 A1 | 8/2006 | Crittenden |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2007/0005131 A1 | 1/2007 | Taylor |
| 2007/0010877 A1 | 1/2007 | Salahieh et al. |
| 2007/0027534 A1 | 2/2007 | Bergheim et al. |
| 2007/0066863 A1 | 3/2007 | Rafiee et al. |
| 2007/0088431 A1 | 4/2007 | Bourang et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0270943 A1 | 11/2007 | Solem et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082166 A1 | 4/2008 | Styrc et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0016958 A1 | 1/2010 | St. Goar et al. |
| 2010/0036479 A1 | 2/2010 | Hill et al. |
| 2010/0049313 A1 | 2/2010 | Alon et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2011/0015616 A1 | 1/2011 | Straubinger et al. |
| 2011/0015729 A1 | 1/2011 | Jimenez et al. |
| 2011/0029072 A1 | 2/2011 | Gabbay |
| 2011/0137397 A1 | 6/2011 | Chau et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0238159 A1 | 9/2011 | Guyenot et al. |
| 2011/0288634 A1 | 11/2011 | Tuval et al. |
| 2011/0319989 A1 | 12/2011 | Lane et al. |
| 2012/0035722 A1 | 2/2012 | Tuval |
| 2012/0046741 A1 | 2/2012 | Tuval et al. |
| 2012/0046742 A1 | 2/2012 | Tuval et al. |
| 2012/0101570 A1 | 4/2012 | Tuval et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0283823 A1 | 11/2012 | Bonhoeffer et al. |
| 2012/0296418 A1 | 11/2012 | Bonyuet et al. |
| 2012/0310336 A1 | 12/2012 | Figulla et al. |
| 2013/0035759 A1 | 2/2013 | Gross et al. |
| 2013/0073035 A1 | 3/2013 | Tuval et al. |
| 2013/0079869 A1 | 3/2013 | Straubinger et al. |
| 2013/0144381 A1 | 6/2013 | Quadri et al. |
| 2013/0190862 A1 | 7/2013 | Pintor et al. |
| 2013/0197622 A1 | 8/2013 | Mitra et al. |

(56) References Cited

U.S. PATENT DOCUMENTS

| | | | |
|---|---|---|---|
| 2014/0194979 | A1 | 7/2014 | Seguin et al. |
| 2014/0277390 | A1 | 9/2014 | Ratz et al. |
| 2014/0330371 | A1 | 11/2014 | Gloss et al. |

FOREIGN PATENT DOCUMENTS

| | | | |
|---|---|---|---|
| DE | 19546692 | A1 | 6/1997 |
| DE | 19857887 | A1 | 7/2000 |
| DE | 19907646 | A1 | 8/2000 |
| DE | 10010074 | A1 | 10/2001 |
| DE | 10049812 | A1 | 4/2002 |
| DE | 10049813 | C1 | 4/2002 |
| DE | 10049814 | A1 | 4/2002 |
| DE | 10049815 | A1 | 4/2002 |
| DE | 102006052564 | B3 | 12/2007 |
| EP | 0103546 | A1 | 3/1984 |
| EP | 0144167 | A2 | 6/1985 |
| EP | 0592410 | A1 | 4/1994 |
| EP | 0597967 | A1 | 5/1994 |
| EP | 0850607 | A1 | 7/1998 |
| EP | 1057460 | A1 | 12/2000 |
| EP | 1088529 | A2 | 4/2001 |
| EP | 1469797 | A1 | 10/2004 |
| EP | 1570809 | A1 | 9/2005 |
| EP | 1653888 | A2 | 5/2006 |
| FR | 2788217 | A1 | 7/2000 |
| FR | 2815844 | A1 | 5/2002 |
| GB | 2056023 | A | 3/1981 |
| SU | 1271508 | A1 | 11/1986 |
| WO | 9117720 | A1 | 11/1991 |
| WO | 9217118 | A1 | 10/1992 |
| WO | 93001768 | A1 | 2/1993 |
| WO | 9724080 | A1 | 7/1997 |
| WO | 98/29057 | A1 | 7/1998 |
| WO | 9933414 | A1 | 7/1999 |
| WO | 99/40964 | A1 | 8/1999 |
| WO | 99/47075 | A1 | 9/1999 |
| WO | 0018333 | A1 | 4/2000 |
| WO | 0041652 | A1 | 7/2000 |
| WO | 0047139 | A1 | 8/2000 |
| WO | 0128459 | A1 | 4/2001 |
| WO | 0135878 | A2 | 5/2001 |
| WO | 0149213 | A2 | 7/2001 |
| WO | 0154624 | A1 | 8/2001 |
| WO | 0154625 | A1 | 8/2001 |
| WO | 0162189 | A1 | 8/2001 |
| WO | 0164137 | A1 | 9/2001 |
| WO | 0176510 | A2 | 10/2001 |
| WO | 0222054 | A1 | 3/2002 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 0249540 | A2 | 6/2002 |
| WO | 03047468 | A1 | 6/2003 |
| WO | 2005034812 | | 4/2005 |
| WO | 2005087140 | A1 | 9/2005 |
| WO | 2006014233 | A2 | 2/2006 |
| WO | 2006034008 | A2 | 3/2006 |
| WO | 06/108090 | | 10/2006 |
| WO | 2006111391 | A1 | 10/2006 |
| WO | 2006138173 | A2 | 12/2006 |
| WO | 2005102015 | A3 | 4/2007 |
| WO | 2008005405 | A2 | 1/2008 |
| WO | 2008035337 | A2 | 3/2008 |
| WO | 2008147964 | A1 | 12/2008 |
| WO | 2008150529 | A1 | 12/2008 |
| WO | 09/024859 | | 2/2009 |
| WO | 09/116041 | | 9/2009 |

OTHER PUBLICATIONS

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.
Al Zaibag, Muayed, et al., "Percutaneous Balloon Valvotomy in Tricuspid Stenosis," British Heart Journal, Jan. 1987, vol. 57, No. 1, pp. 51-53.
Andersen, et al., "Transluminal implantation of artificial heart valves. Description of a new expandable aortic valve and initial results with implantation by catheter technique in closed chest pigs." European Heart Journal (1992), 13, 704-708.
Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.
Dake, Transluminal Placement of Endovascular Stent-Grafts for the Treatment of Descending Thoracic Aortic Aneurysms, New Engl. J.Med., 1994; 331:1729 34.
Dotter, M.D., Charles T., "Transluminal Treatment of Arteriosclerotic Obstruction," University of Oregon's Minthom Memorial Laboratory for Cardiovascular Research through Radiology, Circulation, vol. XXX, Nov. 1964, pp. 654-670.
Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.
Inoue, M.D., Kanji, et al., "Clinical Application of Transvenous Mitral Commissurotomy by a New Balloon Catheter," The Journal of Thoracic and Cardiovascular Surgery 87:394-402, 1984.
Lawrence, Jr., M.D., David D., "Percutaneous Endovascular Graft: Experimental Evaluation," Radiology 1897; 163: 357-360.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W., et al., "Der Verschluß des Ductus Arteriosus Persistens ohne Thorakotomie," Thoraxchirurgie Vaskulare Chirurgie, Band 15, Heft 2, Stuttgart, im Apr. 1967, pp. 199-203.
Rashkind, M.D., William J., "Creation of an Atrial Septal Defect Withoput Thoracotomy," the Journal of the American Medical Association, vol. 196, No. 11, Jun. 13, 1966, pp. 173-174.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Intery Radiol 2003; 14:841-853.
Ross, F.R.C.S., D.N., "Aortic Valve Surgery," Guys Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, Ulrich, "An Overview of Intravascular Stents: Old and New," Chapter 48, Textbook of Interventional Cardiology, 2nd Edition, W.B. Saunders Company, Philadelphia, PA, ©1994, 1990, pp. 803-815.
Uchida, Barry T., et al., "Modifications of Gianturco Expandable Wire Stents," AJR:150, May 1988, Dec. 3, 1987, pp. 1185-1187.
Urban, M.D., Philip, "Coronary Artery Stenting," Editions Medecine et Hygiene, Geneve, 1991, pp. 5-47.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

(56) References Cited

OTHER PUBLICATIONS

Wheatley, M.D., David J., "Valve Prostheses," Rob & Smith's Operative Surgery, Fourth Edition, pp. 415-424, Butterworths 1986.

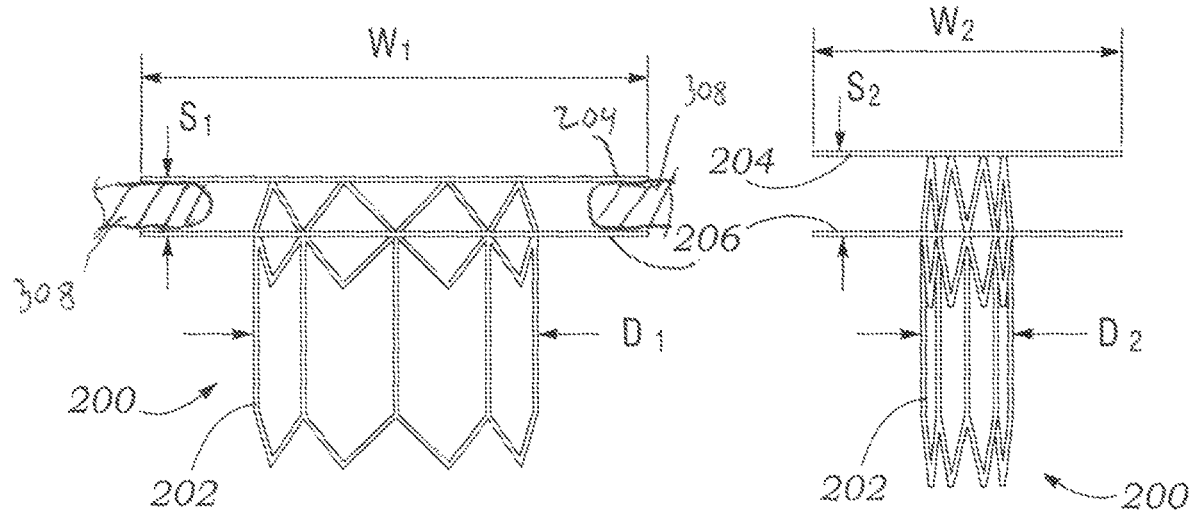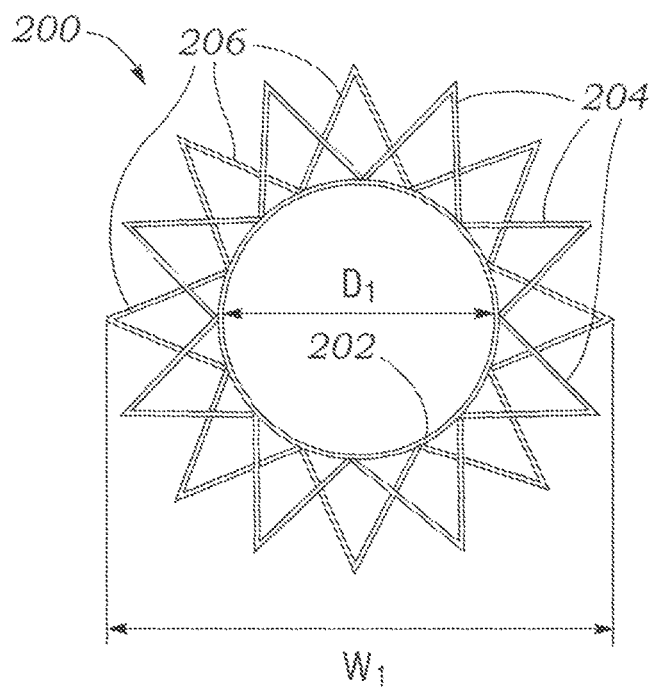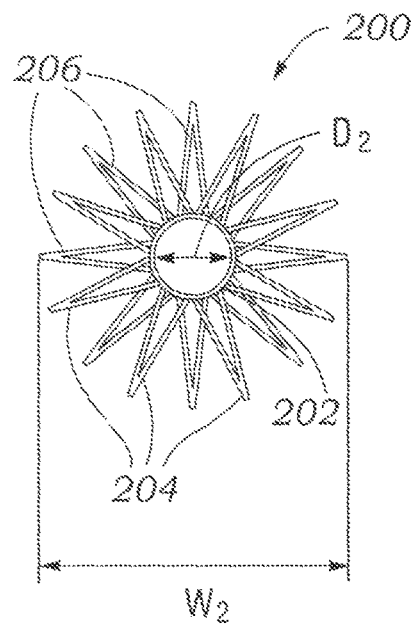

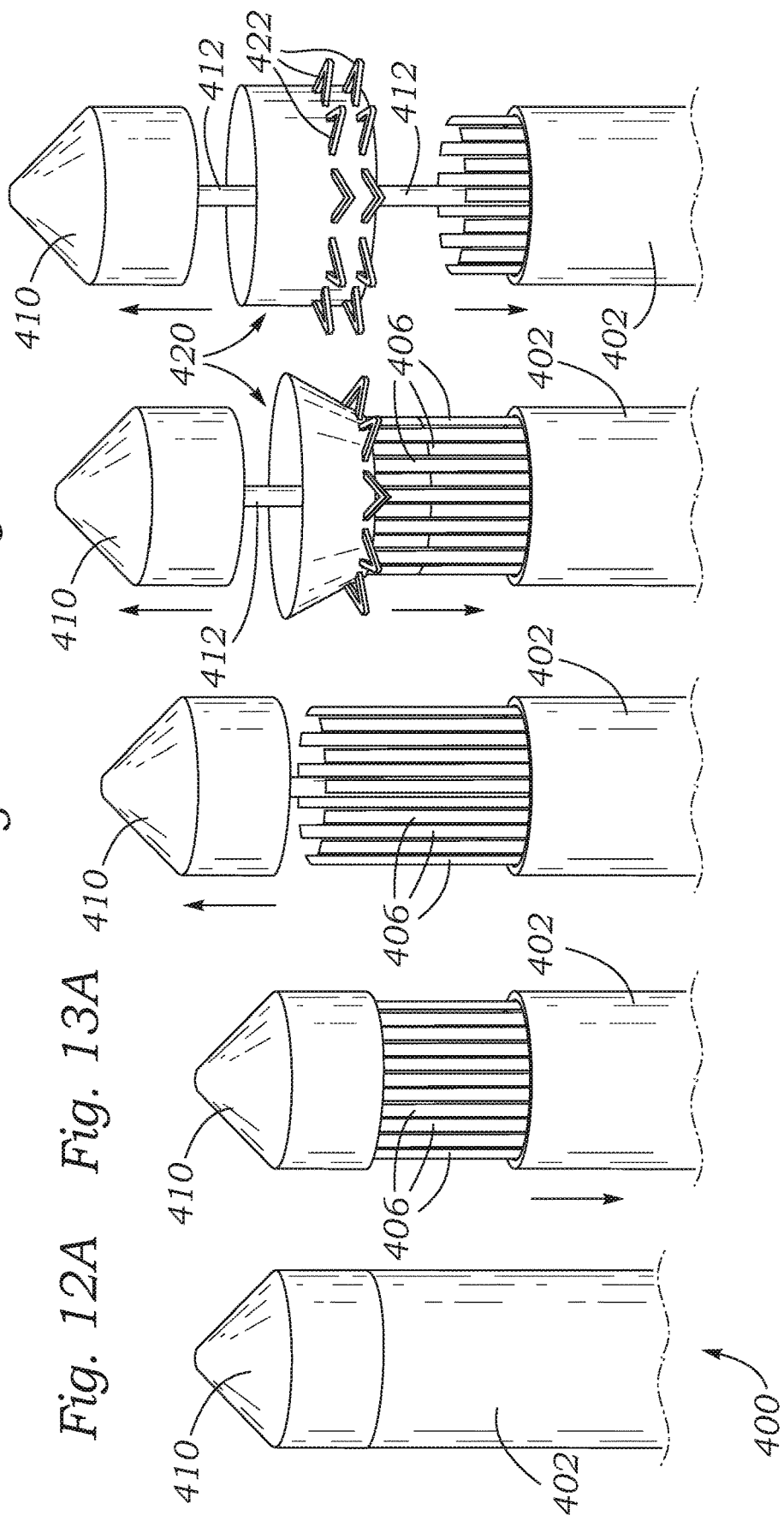

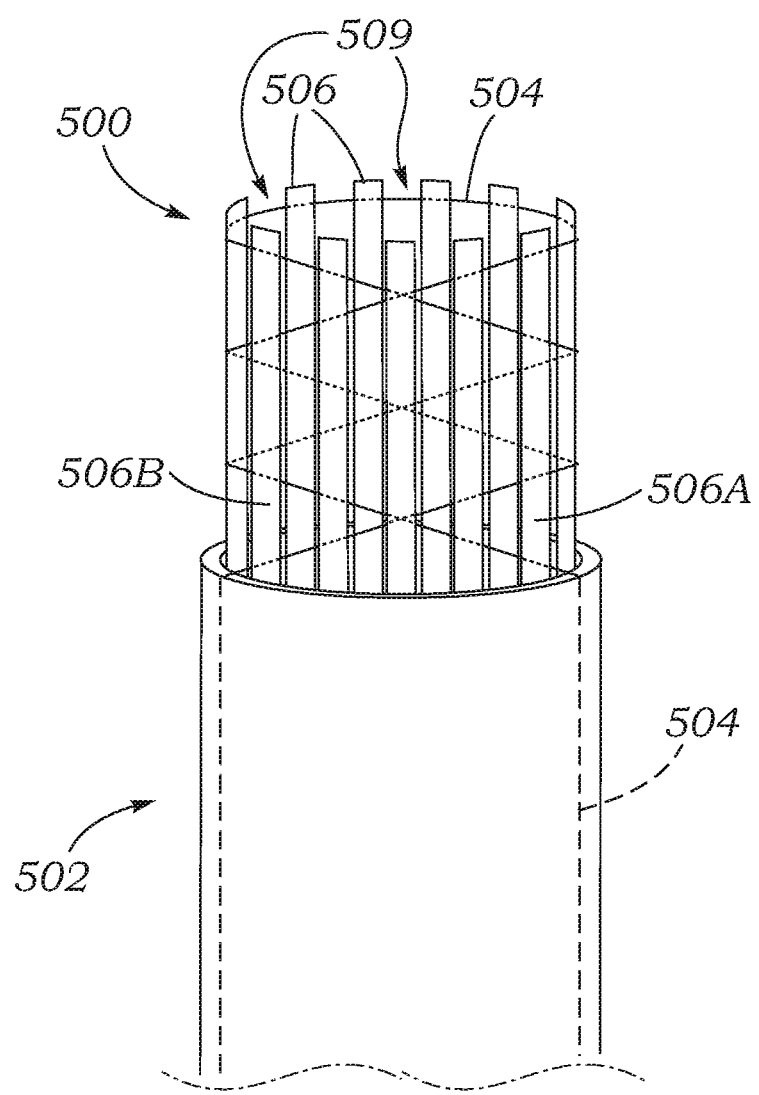

DUAL-FLANGE PROSTHETIC VALVE FRAME

CROSS-REFERENCE TO RELATED APPLICATION

The present application is a continuation of U.S. application Ser. No. 14/830,347, filed Aug. 19, 2015, now U.S. Pat. No. 10,058,424, which claims the benefit of U.S. Provisional Application No. 62/040,099, filed Aug. 21, 2014, which is incorporated herein by reference.

FIELD

The present disclosure relates to implantable devices and, more particularly, to prosthetic valves for implantation into body ducts, such as native-heart-valve annuluses.

BACKGROUND

The human heart can suffer from various valvular diseases, which can result in significant malfunctioning of the heart and ultimately require replacement of the native heart valve with an artificial valve. There are a number of known artificial valves and a number of known methods of implanting these artificial valves in humans.

One method of implanting an artificial heart valve in a human patient is via open-chest surgery, during which the patient's heart is stopped and the patient is placed on cardiopulmonary bypass (using a so-called "heart-lung machine"). In one common surgical procedure, the diseased native valve leaflets are excised and a prosthetic valve is sutured to the surrounding tissue at the native valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure.

Because of the drawbacks associated with conventional open-chest surgery, percutaneous and minimally-invasive surgical approaches are in some cases preferred. In one such technique, a prosthetic valve is configured to be implanted in a much less invasive procedure by way of catheterization. For instance, U.S. Pat. Nos. 7,393,360, 7,510,575, and 7,993,394 describe collapsible transcatheter prosthetic heart valves that can be percutaneously introduced in a compressed state on a catheter and expanded to a functional size at the desired position by balloon inflation or by utilization of a self-expanding frame or stent.

SUMMARY

In some embodiments, an implantable prosthetic valve comprises a radially collapsible and radially expandable, annular, main body defining a lumen therethrough, a first flange coupled to the main body and extending radially away from the main body, the first flange comprising a plurality of radially extending first protrusions, a second flange coupled to the main body and extending radially away from the main body, the second flange comprising a plurality of radially extending second protrusions, and a valve member supported within the lumen of the frame, wherein the first flange and the second flange are closer to one another when the main body is in a radially expanded configuration than when the main body is in a radially collapsed configuration, and wherein each of the first protrusions and each of the second protrusions comprise a first radial strut coupled to a first node of the main body and extending radially away from the main body, a second radial strut coupled to a second node of the main body and extending radially away from the main body, a first angled strut coupled at an angle to the first radial strut, and a second angled strut coupled at an angle to the second radial strut and coupled to the first angled strut.

In some embodiments, the valve member defines an inlet end and an outlet end of the implantable prosthetic valve, and the first flange and the second flange are coupled to the main body at locations located closer to the inlet end than to the outlet end of the implantable prosthetic valve. In some embodiments, the valve member defines an inlet end and an outlet end of the implantable prosthetic valve, and the first flange and the second flange are coupled to the main body at locations located closer to the outlet end than to the inlet end of the implantable prosthetic valve. In some embodiments, the distance between the first flange and the second flange when the prosthetic valve is in the radially collapsed configuration is larger than the thickness of the native human mitral valve annulus, and the distance between the first flange and the second flange when the prosthetic valve is in the radially expanded configuration is smaller than the thickness of the native human mitral valve annulus. In some embodiments, the first protrusions are angularly offset from the second protrusions.

In some embodiments, the main body has a first end and a second end, and comprises a network of struts interconnected at a plurality of nodes to form a plurality of open cells; the first protrusions are coupled to first nodes of the main body at the first end of the main body; and the second protrusions are coupled to second nodes of the main body, which are displaced toward the second end of the main body from the first end of the main body by the smallest increment available. In some embodiments, the main body has a first end and a second end, and comprises a network of struts interconnected at a plurality of nodes to form a plurality of open cells; the first protrusions are coupled to first nodes of the main body at the first end of the main body; and the second protrusions are coupled to second nodes of the main body, the second nodes being the closest nodes in the network of struts to the first nodes. In some embodiments, the main body has a first end and a second end, and comprises a network of struts interconnected at a plurality of nodes to form a plurality of open cells; the first protrusions are coupled to first nodes of the main body at the first end of the main body; and the second protrusions are coupled to second nodes of the main body, the first nodes and the second nodes being situated in a single circumferential row of open cells.

In some embodiments, the first flange extends radially away from the main body such that an angle between a side of the main body and the first flange is between about 70° and about 110°, and the second flange extends radially away from the main body such that an angle between a side of the main body and the second flange is between about 70° and about 110°. In some embodiments, the first flange extends radially away from the main body such that an angle between a side of the main body and the first flange is between about 80° and about 100°, and the second flange extends radially away from the main body such that an angle between a side of the main body and the second flange is between about 80° and about 100°. In some embodiments, the first flange extends radially away from the main body such that an angle between a side of the main body and the first flange is about 90°, and the second flange extends radially away from the main body such that an angle between a side of the main body and the second flange is about 90°.

In some embodiments, the first flange extends radially away from the main body parallel to the second flange. In some embodiments, the first flange and the second flange extend radially away from the main body in directions converging toward one another such that an angle between the radially extending flanges is less than about 10°. In some embodiments, the first flange and the second flange extend radially away from the main body in directions diverging away from one another such that an angle between the radially extending flanges is less than about 10°.

In some embodiments, a method of implanting a prosthetic apparatus at the native mitral valve region of a heart comprises delivering the prosthetic apparatus to the native mitral valve region within a delivery apparatus, and deploying the prosthetic apparatus from the delivery apparatus, wherein the prosthetic apparatus comprises a main body, a first flange coupled to the main body and extending radially away from the main body perpendicular to a side of the main body, and a second flange coupled to the main body and extending radially away from the main body perpendicular to the side of the main body, and wherein deploying the prosthetic apparatus from the delivery apparatus allows the prosthetic apparatus to radially expand, such that a distance between the first flange and the second flange decreases and the first flange and the second flange pinch a native mitral valve annulus between them.

In some embodiments, the prosthetic apparatus has an inlet end and an outlet end, and the first flange and the second flange are coupled to the main body at locations located closer to the inlet end than to the outlet end of the prosthetic apparatus. In some embodiments, the prosthetic apparatus has an inlet end and an outlet end, and the first flange and the second flange are coupled to the main body at locations located closer to the outlet end than to the inlet end of the prosthetic apparatus. In some embodiments, the main body has a first end and a second end, and comprises a network of struts interconnected at a plurality of nodes to form a plurality of open cells; the first flange is coupled to first nodes of the main body at the first end of the main body; and the second flange is coupled to second nodes of the main body, which are displaced toward the second end of the main body from the first end of the main body by the smallest increment available. In some embodiments, the main body has a first end and a second end, and comprises a network of struts interconnected at a plurality of nodes to form a plurality of open cells; the first flange is coupled to first nodes of the main body at the first end of the main body; and the second flange is coupled to second nodes of the main body, the second nodes being the closest nodes in the network of struts to the first nodes. In some embodiments, the main body has a first end and a second end, and comprises a network of struts interconnected at a plurality of nodes to form a plurality of open cells; the first flange is coupled to first nodes of the main body at the first end of the main body; and the second flange is coupled to second nodes of the main body, the first nodes and the second nodes being situated in a single circumferential row of open cells.

The foregoing and other objects, features, and advantages of the invention will become more apparent from the following detailed description, which proceeds with reference to the accompanying figures.

BRIEF DESCRIPTION OF THE DRAWINGS

FIG. 4 illustrates an exemplary prosthetic heart valve frame, in an expanded configuration, from a side view.

FIG. 5 illustrates the exemplary prosthetic heart valve frame of FIG. 4, in a compressed configuration, from a side view.

FIG. 6 illustrates the exemplary prosthetic heart valve frame of FIG. 4, in an expanded configuration, from an end view.

FIG. 7 illustrates the exemplary prosthetic heart valve frame of FIG. 4, in a compressed configuration, from an end view.

FIGS. 12A, 13A, 14A, 15A, and 16A illustrate an exemplary delivery sequence of an exemplary prosthetic heart valve frame using the delivery system of FIGS. 8-11.

FIG. 17A illustrates a slotted sheath having a retaining element.

DETAILED DESCRIPTION

Frames for Use in Prosthetic Valves

Figure 1:
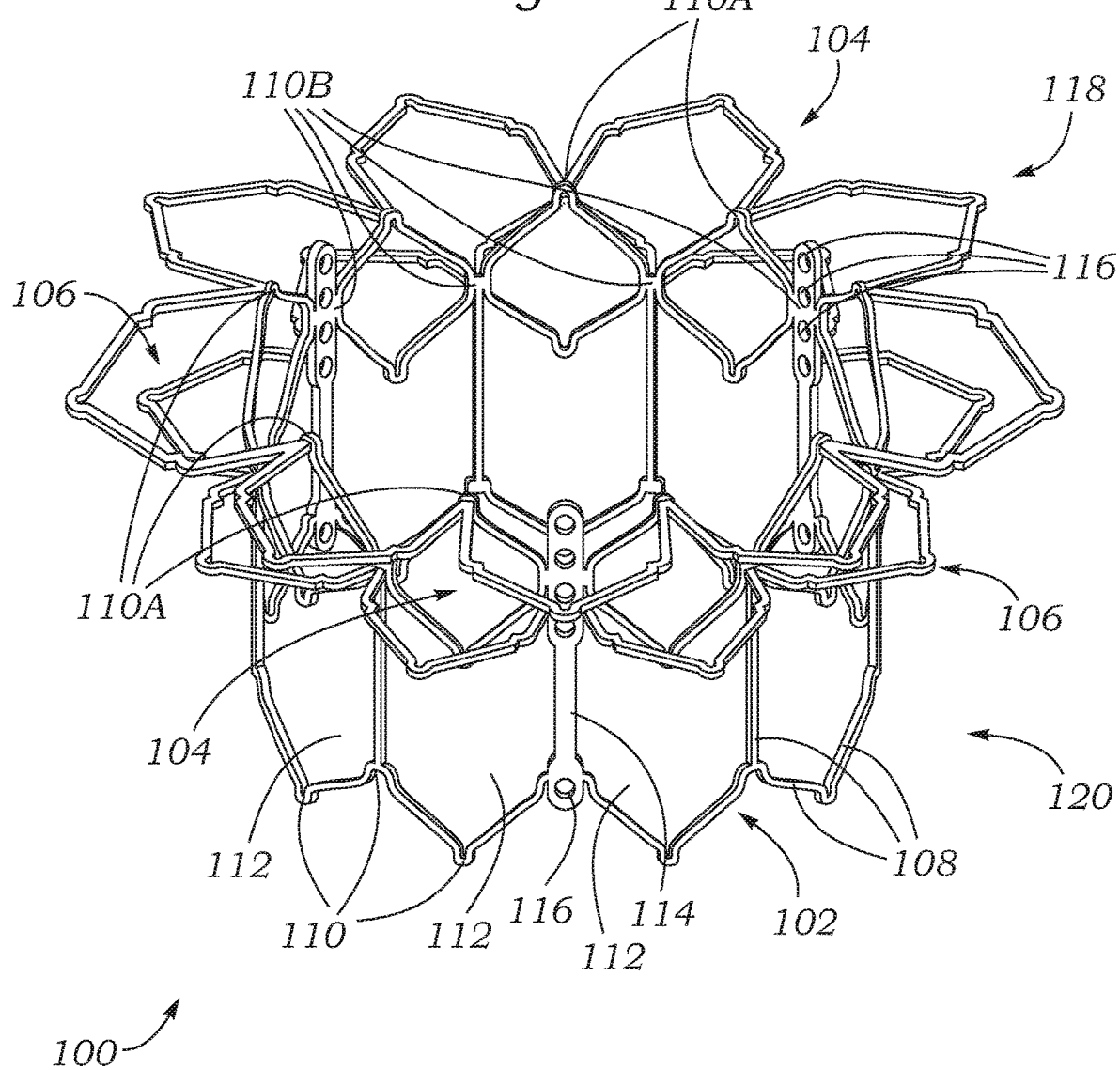
FIG. 1 illustrates an exemplary prosthetic heart valve frame.

The frames described herein can be used to provide structure to prosthetic valves designed to be implanted within the vasculature of a patient. The frames described herein can be particularly advantageous for use in prosthetic valves to be implanted within a patient's native mitral valve, but can be used in prosthetic valves to be implanted in various other portions of a patient's vasculature (e.g., another native valve of the heart, or various other ducts or orifices of the patient's body). When implanted, the frames described herein can provide structural support to a leaflet structure and/or other components of a prosthetic valve such that the prosthetic valve can function as a replacement for a native valve, allowing fluid to flow in one direction through the prosthetic valve from an inlet end to an outlet end, but not in the other or opposite direction from the outlet end to the inlet end. Details of various prosthetic valve components can be found in U.S. Pat. Nos. 6,730,118, 7,393,360, 7,510,575, and 7,993,394, which are hereby incorporated herein by reference in their entireties.

The frames described herein can be configured to be radially collapsible to a collapsed or crimped state for introduction into the body on a delivery catheter and radially expandable to an expanded state for implanting a prosthetic valve at a desired location in the body (e.g., the native mitral valve). The frames can be made of a plastically-expandable material that permits crimping of the prosthetic valve to a smaller profile for delivery and expansion of the prosthetic valve using an expansion device such as the balloon of a balloon catheter. Suitable plastically-expandable materials that can be used to form the frames include, without limitation, stainless steel, cobalt-chromium, nickel-based alloy (e.g., a nickel-cobalt-chromium alloy), polymers, or combinations thereof. In particular embodiments, the frames are made of a nickel-cobalt-chromium-molybdenum alloy, such as MP35N® alloy (SPS Technologies), which is equivalent to UNS R30035 (covered by ASTM F562-02). MP35N® alloy/UNS R30035 comprises 35% nickel, 35% cobalt, 20% chromium, and 10% molybdenum, by weight. It has been found that the use of MP35N® alloy to form a frame provides superior structural results over stainless steel. In particular, when MP35N® alloy is used as the frame material, less material is needed to achieve the same or better performance in radial and crush force resistance, fatigue resistances, and corrosion resistance. Moreover, since less material is required, the crimped profile of the frames can be reduced, thereby providing a lower profile prosthetic valve assembly for percutaneous delivery to the treatment location in the patient's body.

Alternatively, any of the frames described herein can be a so-called self-expanding frame wherein the frame is made of a self-expanding material such as nitinol. A prosthetic valve incorporating a self-expanding frame can be crimped to a smaller profile and held in the crimped state with a restraining device such as a sheath covering the prosthetic valve. When the prosthetic valve is positioned at or near a target site within the patient's vasculature, the restraining device can be removed to allow the prosthetic valve to self-expand to its expanded, functional size.

Figure 2:
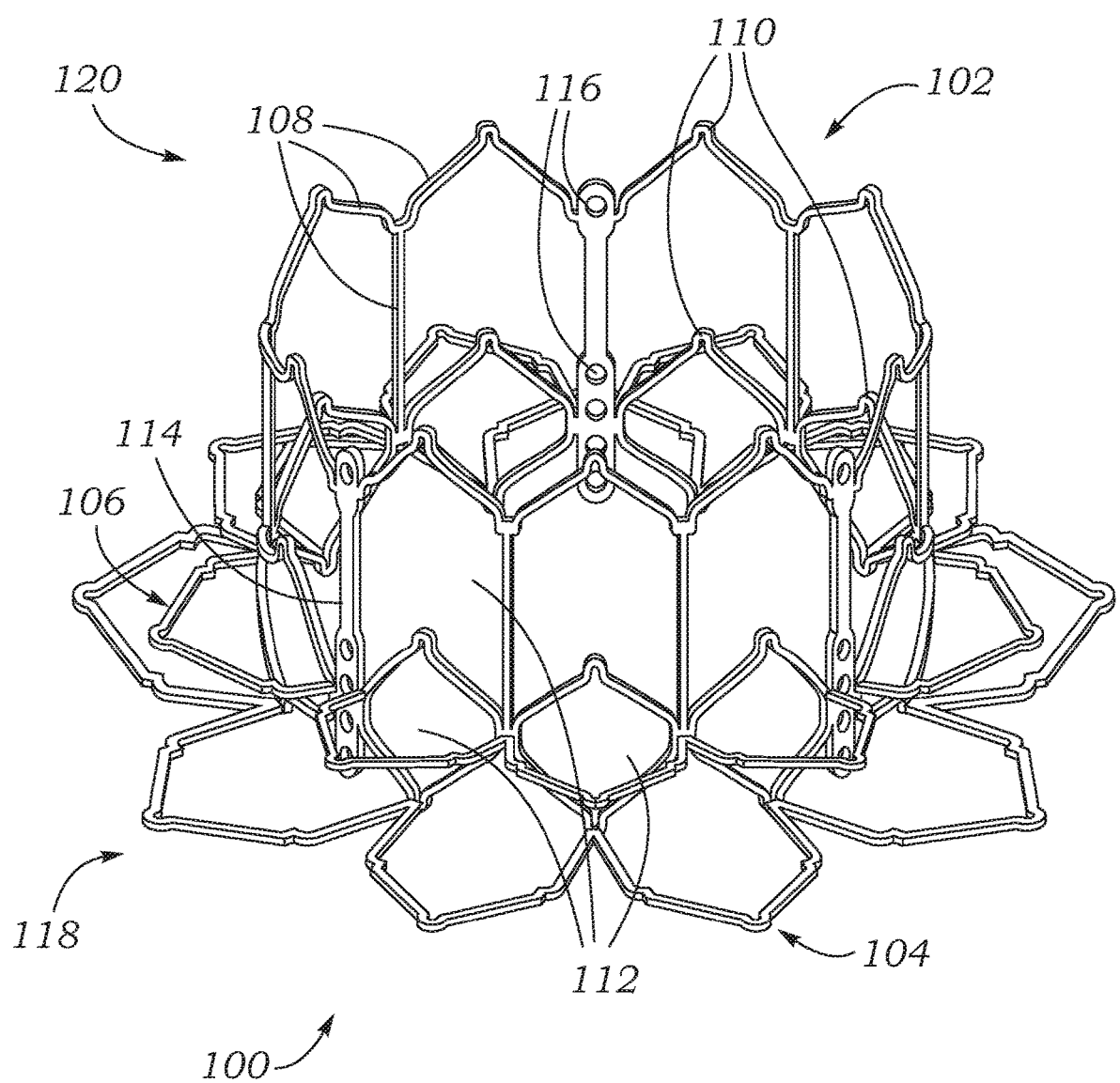
FIG. 2 illustrates the exemplary prosthetic heart valve frame of FIG. 1 from a different angle.
Figure 3:
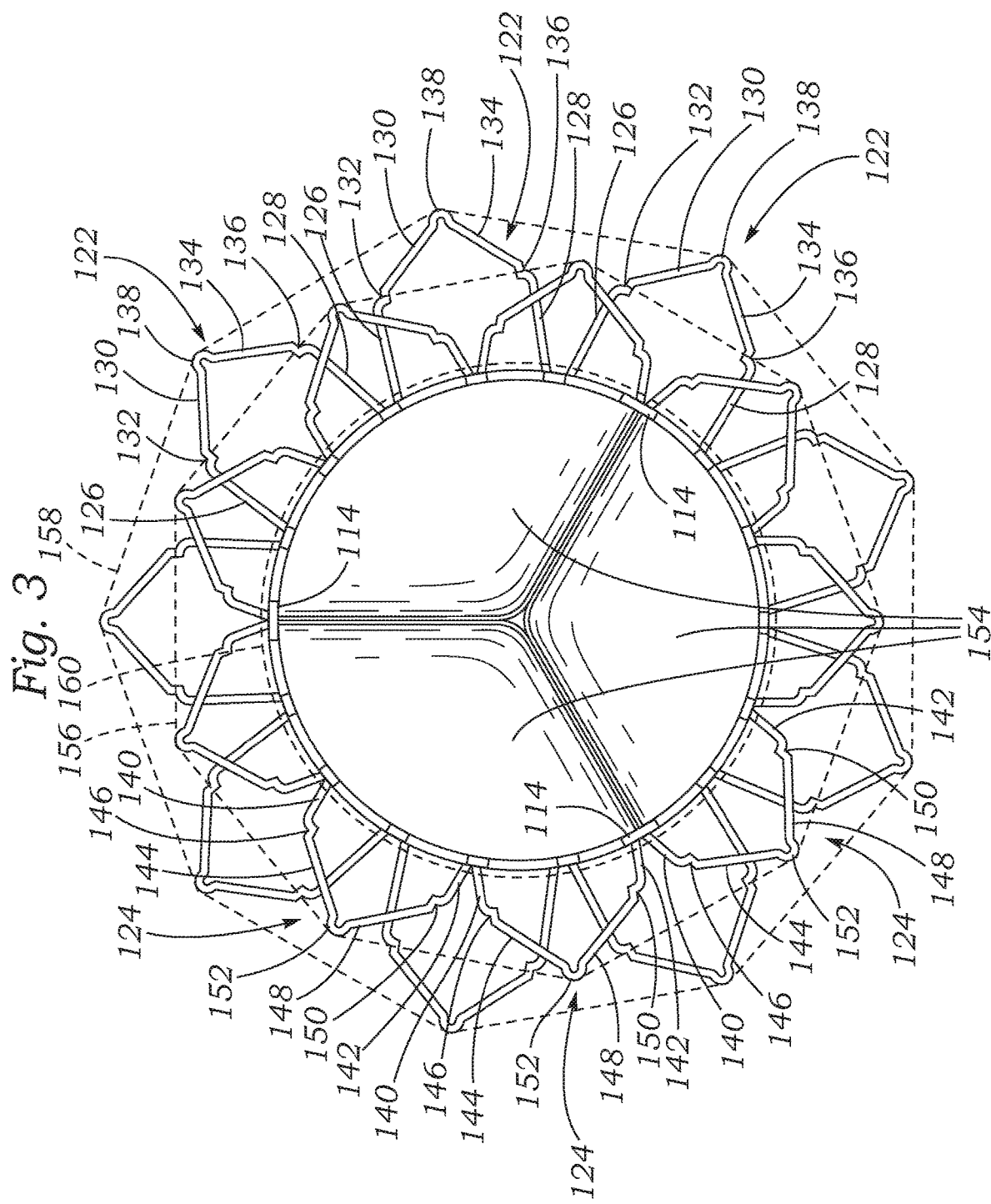
FIG. 3 illustrates the exemplary prosthetic heart valve frame of FIG. 1 from a ventricular end view.

FIGS. 1-3 illustrate an exemplary prosthetic heart valve frame 100. Frame 100 includes a main body 102, a first flange 104, and a second flange 106. The main body 102 can be formed from a plurality of struts 108 coupled to one another at a plurality of nodes 110 to form a network of struts 108 defining a plurality of open cells 112. The main body 102 can have a first end portion 118, which can be referred to as an atrial end portion 118 or an inlet end portion 118, and a second end portion 120, which can be referred to as a ventricular end portion 120 or an outlet end portion 120, and can include three commissure attachment posts 114, each including a plurality of openings 116 to allow other components such as prosthetic valve leaflets to be coupled (e.g., stitched) to the frame 100. Suitable components and methods for coupling the other components to the frame 100 are known in the art. The first flange 104 can be referred to as the atrial flange 104, and the second flange 106 can be referred to as the ventricular flange 106, due to their relative locations with respect to one another and the left atrium and the left ventricle when the frame is implanted in the native mitral valve.

In an alternative embodiment, the first end portion 118 is a ventricular, outlet end portion, the second end portion 120 is an atrial, inlet end portion, the first flange 104 is a ventricular flange, and the second flange 106 is an atrial flange 106.

The main body 102 and flanges 104, 106 have generally circular shapes in the illustrated embodiment. In alternative embodiments, the main body and flanges of a prosthetic mitral valve frame can have non-circular shapes, for example, to accommodate the non-circular shape of the native mitral valve annulus. In certain embodiments, the main body and flanges of a prosthetic mitral valve frame can be generally oval-shaped, ellipse-shaped, kidney-shaped, or D-shaped.

In the illustrated embodiment, the atrial flange 104 and the ventricular flange 106 are coupled to the main body 102 at respective locations located nearer to the atrial end 118 of the main body 102 than to the ventricular end 120. More specifically, the atrial flange 104 is coupled to the nodes 110A of the main body 102 which are closest to the atrial end portion 118 of the main body 102. The ventricular flange 106 is coupled to the nodes 110B of the main body 102 which are displaced toward the ventricular end 120 of the main body 102 from the atrial flange 104 by the smallest increment available. That is, the nodes 110B are the closest nodes 110 in the network of struts 108 to the nodes 110A. In other embodiments, the nodes 110B are not the closest nodes 110 to the nodes 110A, for example, the second closest or third closest nodes, or another set of nodes. In alternative embodiments, the atrial and ventricular flanges 104, 106 can be coupled to the main body 102 at any suitable locations, which need not be at nodes 110. For example, one or both of the flanges 104, 106 can be coupled to the mid-points of struts 108 of the main body 102 rather than to nodes 110.

As shown in FIG. 3, in the illustrated configuration, the atrial flange 104 comprises nine atrial protrusions 122, and the ventricular flange 106 comprises nine ventricular protrusions 124. In alternative embodiments, the atrial flange can comprise more than or fewer than nine atrial protrusions and the ventricular flange can comprise more than or fewer than nine ventricular protrusions. In some embodiments, the atrial and/or the ventricular flange can include at least three, at least four, at least five, at least six, at least seven, at least eight, at least nine, at least ten, at least twelve, at least fifteen, or at least twenty protrusions. In the illustrated embodiment, the atrial protrusions 122 are slightly larger than the ventricular protrusions 124. In alternative embodiments, the protrusions 122, 124 can be about the same size, or the ventricular protrusions 124 can be larger than the atrial protrusions 122. In the illustrated embodiment, the atrial protrusions 122 are angularly offset from the ventricular protrusions 124. In alternative embodiments, the protrusions 122, 124 can be angularly aligned with one another. Other embodiments include at least one set of protrusions 122, 124 that is angularly aligned and at least one set of protrusions 122, 124 that is not angularly aligned. Each atrial protrusion 122 comprises a first radial strut 126 coupled to a node 110A (FIG. 1) and extending radially outward from the main body 102, and a second radial strut 128 coupled to a node 110A and extending radially outward from the main body 102. Each protrusion 122 further comprises a first angled strut 130 coupled to the first radial strut 126 at a node 132, and a second angled strut 134 coupled to the second radial strut 128 at a node 136. Each first angled strut 130 is coupled to each second angled strut 134 at a respective radial node 138.

Each ventricular protrusion 124 similarly comprises a first radial strut 140 coupled to a node 110B (FIG. 1) and extending radially outward from the main body 102, and a second radial strut 142 coupled to a node 110B and extending radially outward from the main body 102. Each protrusion 124 further comprises a first angled strut 144 coupled to the first radial strut 140 at a node 146, and a second angled strut 148 coupled to the second radial strut 142 at a node 150. Each first angled strut 144 is coupled to each second angled strut 148 at a respective radial node 152. Thus, the protrusions 122 and 124 each comprise a series of struts forming a loop coupled to and extending radially away from the main body 102.

The nodes 138 and 152 of the protrusions 122 and 124, respectively, comprise generally U-shaped crown structures or crown portions. Crown structures can each include a horizontal portion extending between and connecting the adjacent ends of the struts such that a gap is defined between the adjacent ends and the crown structure connects the adjacent ends at a location offset from the struts' natural point of intersection. The nodes 132 and 136, and 146 and 150 of the protrusions 122 and 124, respectively, also comprise stepped portions that are shaped to connect the adjacent ends of the struts at a location offset from the struts' natural point of intersection. Crown structures and stepped portions, both individually and in combination, can significantly reduce strain on the frame 100 during crimping and expanding of the frame 100. Further details regarding crown structures are available in U.S. Pat. No. 7,993,394.

Also shown in FIG. 3 are three prosthetic valve leaflets 154 coupled to the frame 100 at the commissure attachment posts 114. FIG. 3 also illustrates that a prosthetic valve can include a first fabric layer 156 covering the ventricular protrusions 124 and a second fabric layer 158 covering the atrial protrusions 122, as well as a third fabric layer 160 covering the main body 102 of the frame 100. The fabric layers can improve the seal formed between the prosthetic valve and the surrounding native tissues of a native heart valve when the prosthetic valve is implanted. The fabric layers 156, 158, 160 can also reduce trauma to native tissues caused by the implantation of the prosthetic valve, and can help to promote tissue ingrowth into the prosthetic valve. The fabric layers 156, 158, 160 can be made from any of various suitable fabrics, including polyethylene terephthalate (PET).

In the illustrated embodiment, the commissure attachment posts 114 are coupled to radial struts 140, 142 of ventricular protrusions 124, but not to radial struts 126, 128 of atrial protrusions 122. Also in the illustrated embodiment, the commissure attachment posts 114 are angularly aligned about a central longitudinal axis of the frame 100 with radial nodes 138 of atrial protrusions 122, but not with radial nodes 152 of ventricular protrusions 124. In alternative embodiments, the commissure attachment posts 114 can be coupled to radial struts 126, 128 of atrial protrusions 122, and angularly aligned about the central longitudinal axis with radial nodes 152 of ventricular protrusions 124.

As explained above, a prosthetic valve frame can be radially collapsible to a collapsed or crimped state for introduction into the body, and radially expandable to an expanded state for implantation at a desired location in the body. FIGS. 4-7 illustrate a frame 200 from side views (FIGS. 4 and 5) and atrial end views (FIGS. 6 and 7) with a main body 202 of the frame 200 in expanded (FIGS. 4 and 6) and crimped (FIGS. 5 and 7) configurations. Frame 200 includes main body 202, an atrial flange 204, and a ventricular flange 206. The main body 202 has a diameter $D_1$ in the expanded configuration and a diameter $D_2$ in the crimped configuration. The flanges 204, 206 have a diameter or width $W_1$ in the expanded configuration of the main body and a diameter or width $W_2$ in the crimped configuration of the main body. In the illustrated embodiments, the flanges 204, 206 have the same widths $W_1$ and $W_2$; as discussed above, in other embodiments, the flanges 204, 206 have different widths. The flanges 204, 206 are spaced apart from one another by a spacing $S_1$ in the expanded configuration and by a spacing $S_2$ in the crimped configuration.

In some embodiments, $S_1$ can be between about 2 mm and about 20 mm, with about 6 mm being one possible specific dimension. In some embodiments, $S_2$ can be between about 4 mm and about 30 mm, with about 12 mm being one possible specific dimension. In some embodiments, $W_1$ can be between about 30 mm and about 75 mm, with about 55 mm being one possible specific dimension. In some embodiments, $W_2$ can be between about 10 mm and about 60 mm, with about 45 mm being one possible specific dimension. In some embodiments, $D_1$ can be between about 25 mm and about 50 mm, with about 29 mm being one possible specific dimension. In some embodiments, $D_2$ can be between about 4 mm and about 10 mm, with about 6.5 mm being one possible specific dimension.

As illustrated in FIGS. 4-7, as the main body of the frame 200 collapses from the expanded configuration to the crimped configuration, the diameter of the main body 202 decreases significantly (from $D_1$ to $D_2$), the width of the flanges 204, 206 decreases (from $W_1$ to $W_2$), and the spacing between the flanges 204, 206 increases (from $S_1$ to $S_2$). Further, as the main body of the frame 200 collapses from the expanded configuration to the crimped configuration, the protrusions making up the flanges 204, 206 are compressed angularly such that they transition from a series of relatively wide-and-short radially-extending protrusions to a series of relatively narrow-and-long radially-extending protrusions. As shown in FIGS. 4, 5, and 6, an angle between the main body 202 and the radially extending flanges 204, 206 can be about 90° so that a tip of each of the atrial protrusions of the atrial flange 204 points in a direction that is substantially orthogonal to a central axis of the body and a tip of each of the ventricular protrusions of the ventricular flange 206 points in a direction that is substantially orthogonal to the central axis of the body. In alternative embodiments, an angle between the side of the main body 202 and the radially extending flanges 204, 206, can be between about 80° and about 100°, or between about 70° and about 110°, or between about 60° and about 120°.

As shown in FIGS. 4 and 5, the radially extending flanges 204, 206 can extend away from the main body 202 in directions generally parallel to one another. In alternative embodiments, the radially extending flanges 204, 206 can extend away from the main body 202 in directions converging toward one another such that an angle between the radially extending flanges is less than about 1°, or less than about 2°, or less than about 5°, or less than about 10°, or less than about 15°, or less than about 20°, or less than about 25°, or less than about 30°. In other embodiments, the radially extending flanges 204, 206 can extend away from the main body 202 in directions diverging away from one another such that an angle between the radially extending flanges is less than about 1°, or less than about 2°, or less than about 5°, or less than about 10°, or less than about 15°, or less than about 20°, or less than about 25°, or less than about 30°.

Figure 18:
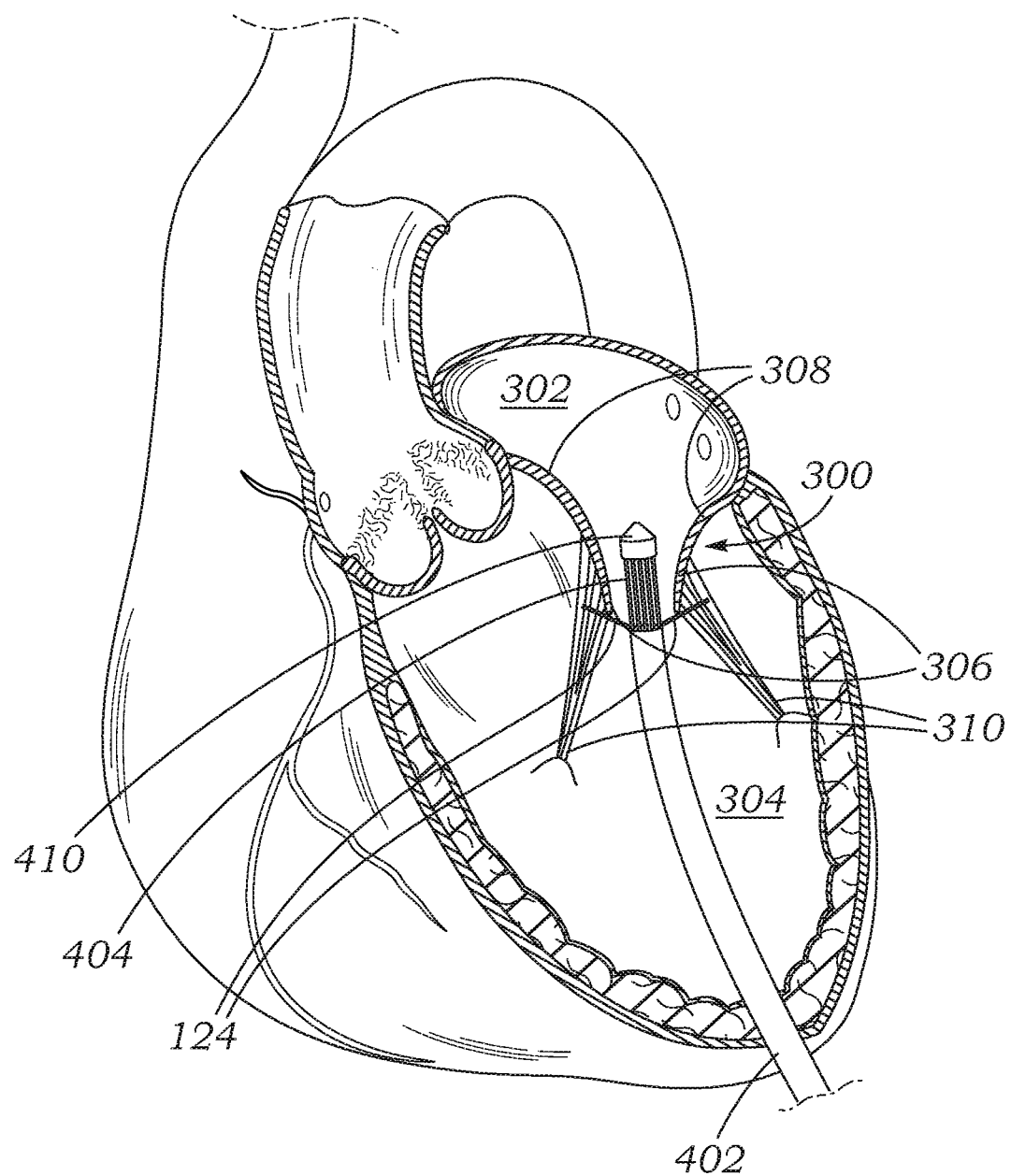
FIG. 18 illustrates a transventricular delivery approach.

The frame 200 can be used as the frame of a prosthetic valve to be implanted at the native mitral valve of a human heart. As shown in FIG. 18, the native mitral valve 300 of the human heart connects the left atrium 302 to the left ventricle 304. The native mitral valve 300 includes a native mitral valve annulus 308, which is an annular portion of native tissue surrounding the native mitral valve orifice, and a pair of leaflets 306 coupled to the native mitral valve annulus 308 and extending ventricularly from the annulus 308 into the left ventricle 304. As described in more detail below, in one exemplary method, a prosthetic valve including the frame 200 can be compressed to a crimped configuration, loaded into a delivery system, and introduced into the region of the native mitral valve of a patient's heart. With the frame in the crimped configuration and thus the spacing between the atrial and ventricular flanges 204, 206 maximized, the prosthetic valve can be positioned so that the native mitral valve annulus 308 is situated between the flanges 204, 206 such that the commissure support posts extend below the native mitral valve and support the leaflets of the valve member below the ventricular flange 206 within the left ventricle of the heart (see FIG. 4). The prosthetic valve can then be expanded to the expanded configuration such that the spacing between the flanges 204, 206 is reduced to less than the native thickness of the native mitral valve annulus 308. The flanges 204, 206 can then retain the prosthetic valve in place in the native mitral valve by compressing or pinching the annulus 308 (see FIG. 4). By pinching the native mitral valve annulus, the flanges 204, 206 can also maintain a continuous seal between the native tissue and the prosthetic valve around the exterior of the prosthetic valve, thereby preventing blood from flowing between the outside of the prosthetic valve and the surrounding annulus, and allowing the prosthetic valve to control the flow of blood between the left atrium and the left ventricle.

This method takes advantage of the relative movement of the nodes of the prosthetic valve frame in a direction aligned with the central longitudinal axis of the prosthetic valve. In particular, as a prosthetic valve frame such as frame 100 or frame 200 is radially expanded, nodes aligned with one another along an axis parallel to the central longitudinal axis move toward one another. Thus, by coupling a pair of flanges such as flanges 104 and 106, or flanges 204 and 206 to nodes spaced apart from each other axially, the flanges can be made to approach one another as the prosthetic valve expands.

Delivery Systems and Methods

Figure 8:
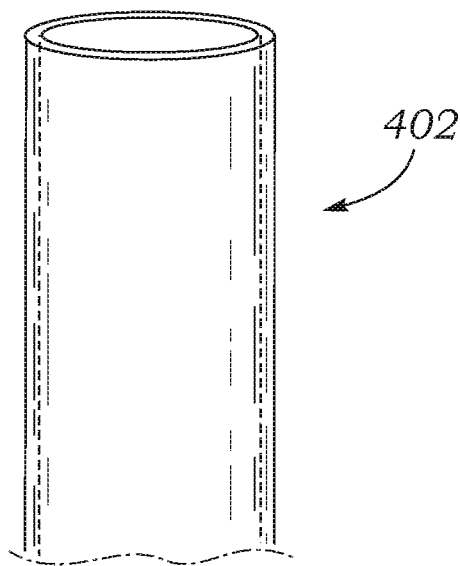
FIG. 8 illustrates an outer sheath of an exemplary delivery system.
Figure 9:
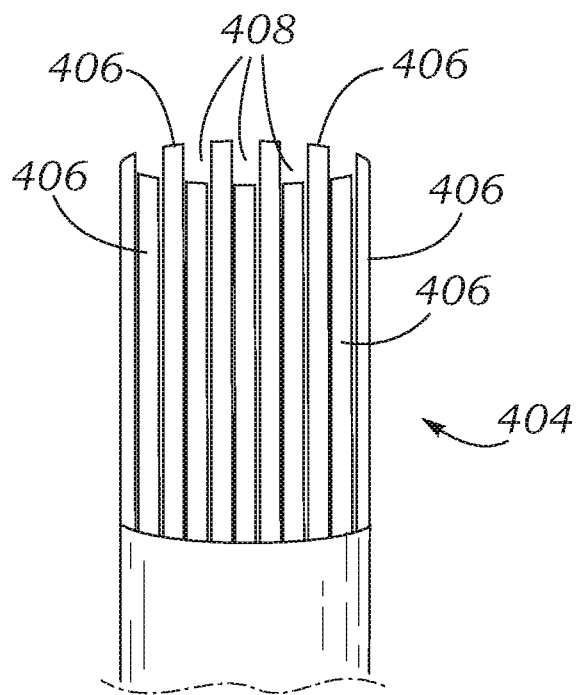
FIG. 9 illustrates a slotted sheath of an exemplary delivery system.

FIGS. 8-11 illustrate components of an exemplary delivery system 400 (FIGS. 12A-16A) which can be used to deliver a prosthetic valve including a frame such as frame 100 or frame 200 to a native heart valve. FIG. 8 illustrates an outer sheath 402 of the delivery system 400. Outer sheath 402 is a hollow sheath which surrounds the remaining components of the delivery system 400 and the prosthetic valve being delivered. FIG. 9 illustrates a slotted sheath 404 of the delivery system 400. Slotted sheath 404 includes a plurality of distal extensions 406 separated by a plurality of distal slots 408. In some embodiments, the slotted sheath 404 can include at least three, at least four, at least five, at least six, at least seven, at least eight, at least nine, at least ten, at least twelve, at least fifteen, or at least twenty slots 408. In some embodiments, the number of slots 408 in the slotted sheath 404 can correspond to a number of atrial protrusions, and/or a number of ventricular protrusions in a frame of a prosthetic valve, and/or a sum of the number of atrial protrusions and the number of ventricular protrusions. Slotted sheath 404 has an outside diameter slightly smaller than the inside diameter of the outer sheath 402 so that the slotted sheath 404 can fit within the outer sheath 402.

Figure 10:
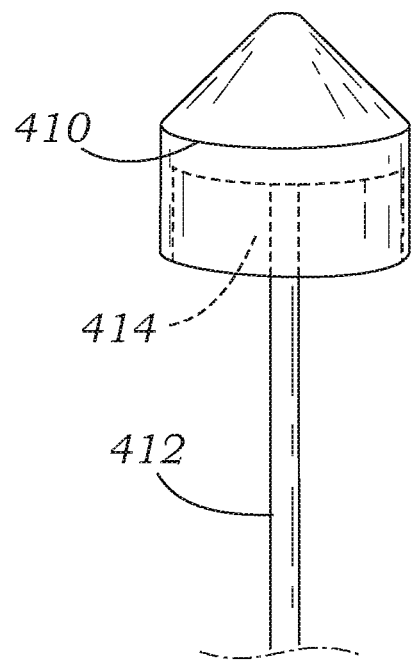
FIG. 10 illustrates a nosecone of an exemplary delivery system.
Figure 11:
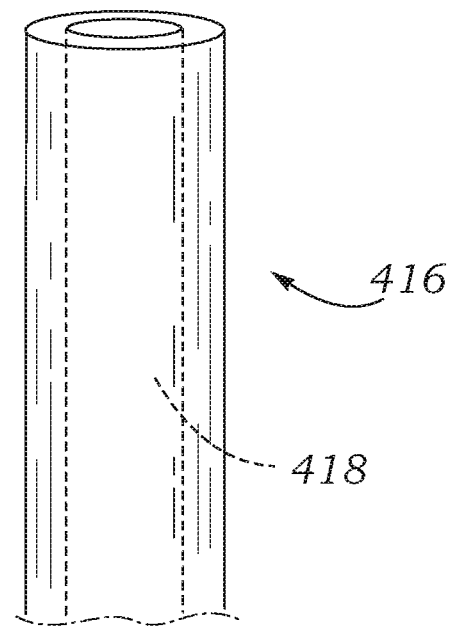
FIG. 11 illustrates an inner pusher shaft of an exemplary delivery system.

FIG. 10 illustrates a nosecone 410 coupled to an inner shaft 412 of the delivery system 400. The nosecone is hollow and includes an inner recess 414. The nosecone 410 can have an outer diameter matching that of the outer sheath 402, and the recess 414 can have a diameter slightly larger than the outer diameter of the slotted sheath 404 so that a distal end portion of the slotted sheath 404 can fit within the recess 414. FIG. 11 illustrates an inner pusher shaft 416 of the delivery system 400. The pusher shaft 416 can have an outside diameter smaller than an inside diameter of the slotted sheath 404 so that the pusher shaft 416 can fit within the slotted sheath 404. The pusher shaft 416 can also have an internal lumen 418 through which the inner shaft 412 can fit. When assembled, the delivery system 400 can include, from center to exterior, the inner shaft 412, the pusher shaft 416, the slotted sheath 404, and the outer sheath 402.

FIGS. 12A, 13A, 14A, 15A, and 16A illustrate an exemplary delivery sequence of a radially self-expanding prosthetic heart valve frame 420 from delivery system 400. FIG. 12A illustrates the delivery system 400 in a closed, delivery configuration in which the frame 420 is retained within the system 400 (the prosthetic valve can be retained in a radially compressed state within an annular space defined between the slotted sheath 404 and the inner shaft 412 and the nosecone 410). As shown in FIG. 13A, the outer sheath 402 can be retracted proximally to expose the distal extensions 406 of the slotted sheath 404. As shown in FIG. 14A, the inner shaft 412 and nosecone 410 can be extended distally to expose the distal end portion of the slotted sheath 404.

As shown in FIG. 15A, the inner shaft 412 and nosecone 410 can be further extended distally to provide sufficient space for the prosthetic valve frame 420 to be pushed out of the slotted sheath 404. The pusher shaft 416 can then be extended distally while the slotted sheath 404 is retracted proximally so that the prosthetic valve frame 420 is pushed distally through the slotted sheath 404 until the prosthetic valve frame 420 becomes partially exposed and begins to radially self-expand. As shown in FIG. 16A, the inner shaft 412 and nosecone 410 can be further extended distally to provide additional space for the prosthetic valve frame 420 to be pushed out of the slotted sheath 404. The pusher shaft 416 can then be further extended distally while the slotted sheath 404 is further retracted proximally so that the prosthetic valve frame 420 is pushed distally through the slotted sheath 404 until the prosthetic valve frame 420 becomes completely exposed from the system 400 and radially self-expands to a fully expanded configuration.

In an alternative embodiment, the protrusions of a flange of a prosthetic valve frame, such as the protrusions of flanges 104, 106, 204, or 206, or protrusions 422 of prosthetic valve frame 420, can fit within or extend through the distal slots 408 of the slotted sheath 404. As described above, as prosthetic valve frames 100, 200, 420 are compressed to a crimped configuration, the respective protrusions are compressed angularly such that they transition from a series of relatively wide and short, radially-extending protrusions to a series of relatively narrow and long, radially-extending protrusions. Thus, the protrusions can be configured to fit within the distal slots 408 when a frame is in the crimped configuration. In this embodiment, loading a prosthetic valve into a delivery system can include crimping the prosthetic valve to a compressed configuration, inserting the compressed prosthetic valve into the slotted sheath 404 such that the angularly compressed protrusions fit within the distal slots 408 of the slotted sheath 404, and then adjusting the protrusions so they lie flat against the outside of the slotted sheath 404, or so they lie flat within the slots 408 and against the outside of the main body of the prosthetic valve, so the prosthetic valve and slotted sheath 404 can be contained within the outer sheath 402 and recess 414 of the nosecone 410. The protrusions of one of the flanges can be contained within the nosecone 410, and the protrusions of the other flange can be contained within the outer sheath 402. Adjusting the protrusions so they lie flat against the outside of the slotted sheath, or so they lie flat within the slots 408 and against the outside of the main body of the prosthetic valve, can include bending the protrusions of the atrial flange so they point either toward or away from the protrusions of the ventricular flange, and bending the protrusions of the ventricular flange so they point either toward or away from the protrusions of the atrial flange.

Figure 12B:
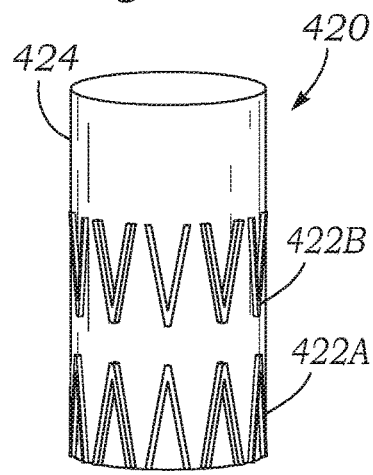
FIGS. 12B, 13B, 14B, 15B, and 16B illustrate an exemplary delivery sequence of an exemplary prosthetic heart valve frame.
Figure 13B:
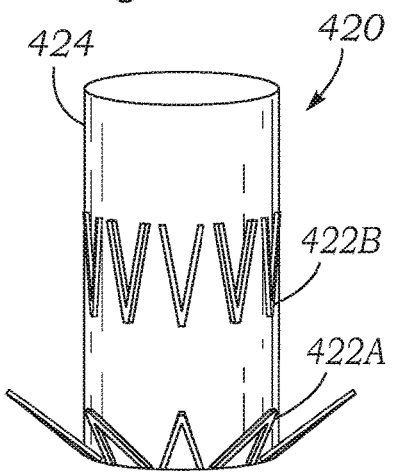
Figure 14B:
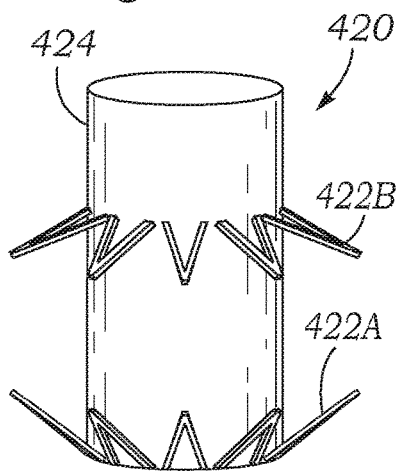

FIGS. 12B, 13B, 14B, 15B, and 16B illustrate an exemplary delivery sequence of the prosthetic heart valve frame 420 from the delivery system 400. FIG. 12B shows the frame 420 in a compressed configuration with protrusions 422A and 422B lying flat against a main body 424 of the frame 420, such that the frame 420 can be situated within the delivery system 400 in the configuration shown in FIG. 12A. FIG. 13B shows the main body 424 of the frame 420 in a compressed configuration with protrusions 422B lying flat against the main body 424 of the frame 420, and with the protrusions 422A extending radially outward from the main body 424 of the frame 420, such that the frame 420 can be situated within the delivery system 400 and the protrusions 422A can extend through the slots 408 of the delivery system 400 in the configuration shown in FIG. 13A. FIG. 14B shows the main body 424 of the frame 420 in a compressed configuration with protrusions 422A and the protrusions 422B extending radially outward from the main body 424 of the frame 420, such that the frame 420 can be situated within the delivery system 400 and the protrusions 422A, 422B can extend through the slots 408 of the delivery system 400 in the configuration shown in FIG. 14A.

Figure 15B:
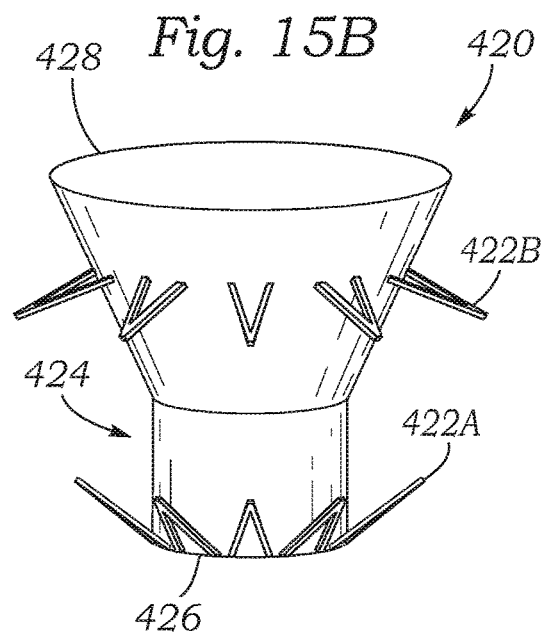
Figure 16B:
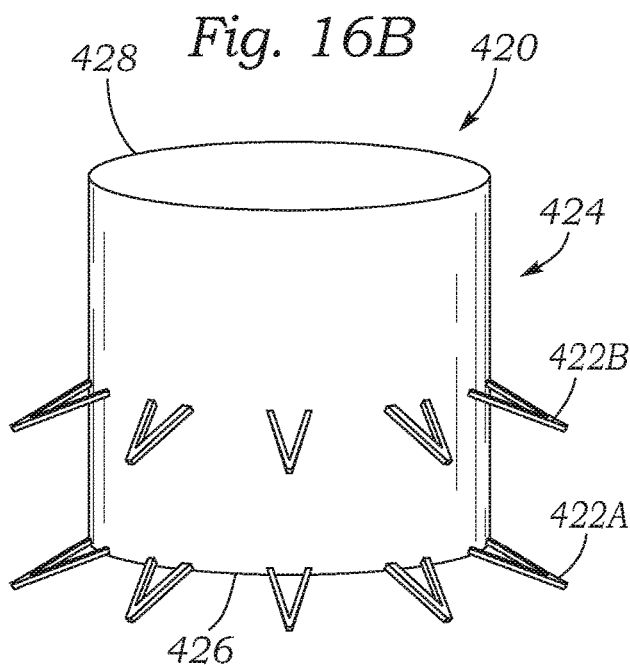

FIG. 15B shows the main body 424 of the frame 420 in a partially expanded configuration in which a first end 426 of the frame 420 is in a compressed configuration and a second end 428 of the frame 420 is in an expanded configuration, such that the frame 420 can be situated within the delivery system 400 in the configuration shown in FIG. 15A. FIG. 16B shows the main body 424 of the frame 420 in a fully expanded configuration in which the first end 426 and the second end 428 are in expanded configurations, such that the frame 420 can be situated on the delivery system 400 in the configuration shown in FIG. 16A.

FIG. 17A illustrates an exposed distal end portion of a slotted sheath 500 having a plurality of distal extensions 506, an outer sheath 502, and a retaining element 504. Small holes extend through the distal extensions 506 so that the retaining element 504, which can be wire, string, and/or suture, can be threaded through the holes. In some cases, the retaining element 504 can extend from a proximal end portion of the outer sheath 502, where it can be controlled by a physician, along the length of the outer sheath 502, and into a first hole through a first distal extension 506A. The retaining element 504 can then be threaded through the holes of successive distal extensions 506 in a coiled or helical configuration until it extends out of a final hole through a final distal extension 506B. In an alternative embodiment, a retaining element can extend into the first hole of the first distal extension 506A, extend through the holes of successive distal extensions 506 in a plurality of circles, and extend out of the final hole of the final distal extension 506B. In some cases, a tension force can be applied to the retaining element 504. The retaining element 504 can help to restrain the distal extensions 506 against radial expansion from the expansion force of a prosthetic valve retained within the extensions 506.

Figure 17B:
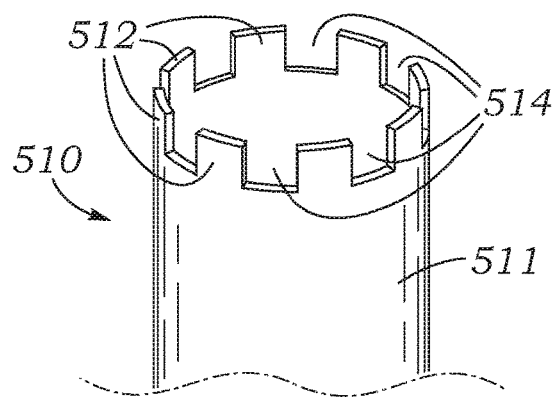
FIGS. 17B-17C illustrate an alternative retaining element.
Figure 17C:
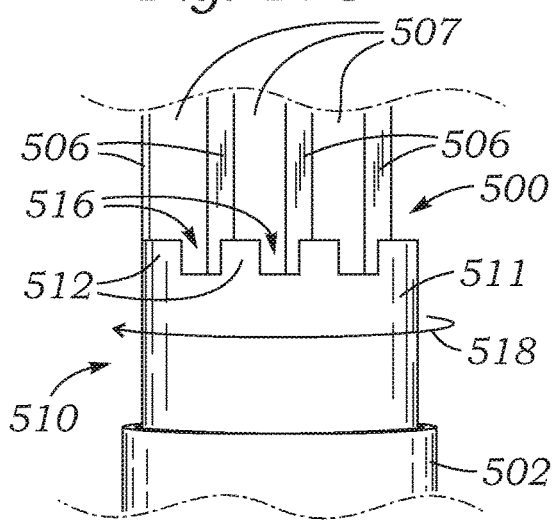

FIGS. 17B-17C illustrate an alternative retaining element 510 which can be used in combination with the outer sheath 502, slotted sheath 500, and distal extensions 506, either in place of, or in addition to, the retaining element 504. Retaining element 510 includes a sheath 511 having a distal end portion comprising a plurality of teeth 512 and a plurality of gaps 514 between the teeth 512. In use in a delivery system including outer sheath 502, slotted sheath 500, and distal extensions 506, as shown in FIG. 17C, the retaining element 510 can be situated between the outer sheath 502 and the slotted sheath 500. The teeth 512 can have a one-to-one correspondence with the distal extensions 506, and each tooth 512 can be rotationally offset with respect to a respective distal extension 506 so as to form a protrusion-receiving opening 516.

Loading a prosthetic valve including a frame such as frame 100, frame 200, or frame 420 into the delivery system can proceed according to similar methods, but is described herein with reference to frame 420 for convenience. Loading a prosthetic valve including frame 420 into the delivery system can include crimping the prosthetic valve to a compressed configuration, in which the protrusions 422A, 422B of the frame are angularly compressed, as described above. The compressed prosthetic valve can then be inserted into the slotted sheath 500 such that the angularly compressed protrusions 422A, 422B fit within slots 507 between the extensions 506, such that the protrusions 422A are proximal to the protrusions 422B, and such that the proximal set of angularly compressed protrusions 422A extend through the slots 507 and the openings 516. The retaining element 510 can then be rotated in the opposite direction shown by arrow 518, so as to pinch the proximal set of angularly compressed protrusions 422A between the teeth 512 and the extensions 506. The angularly compressed protrusions 422A and 422B can then be adjusted so they lie flat against the outside of the slotted sheath 500, or so they lie flat within the slots 507 and against the outside of the main body 424 of the prosthetic valve frame 420. The outer sheath 502 can then be actuated to move distally with respect to the slotted sheath 500 to enclose the slotted sheath 500, the retaining element 510, and the prosthetic valve.

Deployment of the prosthetic valve from the delivery system can generally progress as described above with reference to FIGS. 12A-16A and 12B-16B, and can include proximally retracting the outer sheath 502 with respect to the slotted sheath 500 to reveal the slotted sheath 500 and the prosthetic valve, such that the angularly compressed protrusions 422A, 422B extend radially outward through the slots 507 between the extensions 506 and the proximal angularly compressed protrusions 422A extend radially through the openings 516. A pusher shaft of the delivery system can then be actuated to push the prosthetic valve distally through the slotted sheath 500, and the retaining element 510 can be actuated to move distally over the slotted sheath 500 with the prosthetic valve. In this way, the proximal set of angularly compressed protrusions 422A can remain pinched between the teeth 512 and the extensions 506 as the prosthetic valve is deployed. When the prosthetic valve approaches the distal end of the extensions 506, the retaining element 510 can be rotated, for example, in the direction shown by the arrow 518 (FIG. 17C), such that it no longer pinches or holds (e.g., it releases) the proximal protrusions 422A. In some cases, releasing the proximal protrusions 422A in this way allows the proximal protrusions 422A to more fully radially extend outward through the openings 516. Thus, while the distal and proximal protrusions 422B, 422A are deployed, the main body 424 remains in a radially compressed state within the slotted sheath 500. In some cases, the retaining element 510 can then be retracted proximally with respect to the prosthetic valve to allow a controlled expansion of the prosthetic valve and a controlled release of the prosthetic valve from the extensions 506. As the main body 424 is deployed, the distal and proximal protrusions 422B, 422A can slide axially in the distal direction through the distal openings 509 of the slots 507.

The retaining element 510 can provide substantial benefits to the delivery system. For example, the retaining element 510 can help to restrain the distal extensions 506 against radial expansion from the expansion force of the prosthetic valve retained within the extensions 506. In particular, as the prosthetic valve moves distally through the extensions 506, the extensions 506 can tend to splay farther and farther apart. The retaining element can help to reduce this effect by maintaining a ring of material (e.g., the distal end portion of the sheath 511) in proximity to the proximal end of the prosthetic valve as the prosthetic valve moves through the extensions 506. This can provide an operator with a greater degree of control over the delivery system and the deployment of the prosthetic valve therefrom.

Figure 17D:
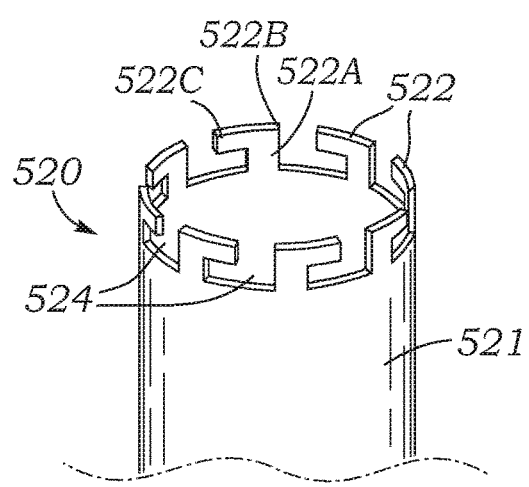
FIGS. 17D-17E illustrate another alternative retaining element.
Figure 17E:
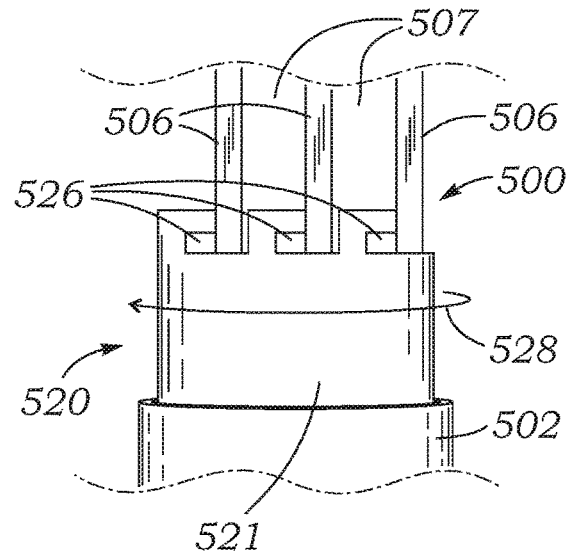

FIGS. 17D-17E illustrate an alternative retaining element 520 which can be used in combination with the outer sheath 502, slotted sheath 500, and distal extensions 506, either in place of, or in addition to, the retaining element 504. Retaining element 520 includes a sheath 521 having a distal end portion comprising a plurality of L-shaped teeth 522 and gaps 524 between the teeth 522. The L-shaped teeth 522 can include a longitudinal portion 522A, a corner portion 522B, and a circumferential portion 522C. In use in a delivery system including outer sheath 502, slotted sheath 500, and distal extensions 506, as shown in FIG. 17E, the retaining element 520 can be situated between the outer sheath 502 and the slotted sheath 500. The teeth 522 can have a one-to-one correspondence with the distal extensions 506, and each tooth 522 can be rotationally offset with respect to a respective distal extension 506 so as to form an enclosed, protrusion-receiving opening 526.

Loading a prosthetic valve including a frame such as frame 100 or frame 200 into the delivery system can generally progress as described above, and such that a proximal set of angularly compressed protrusions 422A of a prosthetic valve frame fit within the openings 526. The retaining element 520 can be rotated in the opposite direction shown by arrow 528 so as to capture the proximal set of angularly compressed protrusions 422A in the enclosed openings 526. Deployment of the prosthetic valve from the delivery system can generally progress as described above. When the prosthetic valve approaches the distal end of the extensions 506, the retaining element 520 can be rotated in the direction shown by the arrow 528 such that it no longer captures or constrains (e.g., it releases) the proximal protrusions 422A.

The retaining element 520 can provide substantial benefits to the delivery system, as described above with regard to retaining element 510. In some cases, the retaining element 510 can be easier to manufacture than the retaining element 520. In some cases, the retaining element 520 provides better performance than the retaining element 510 because the teeth form enclosed openings and capture the proximal protrusions rather than pinching the proximal protrusions.

Delivery Approaches

Figure 19:
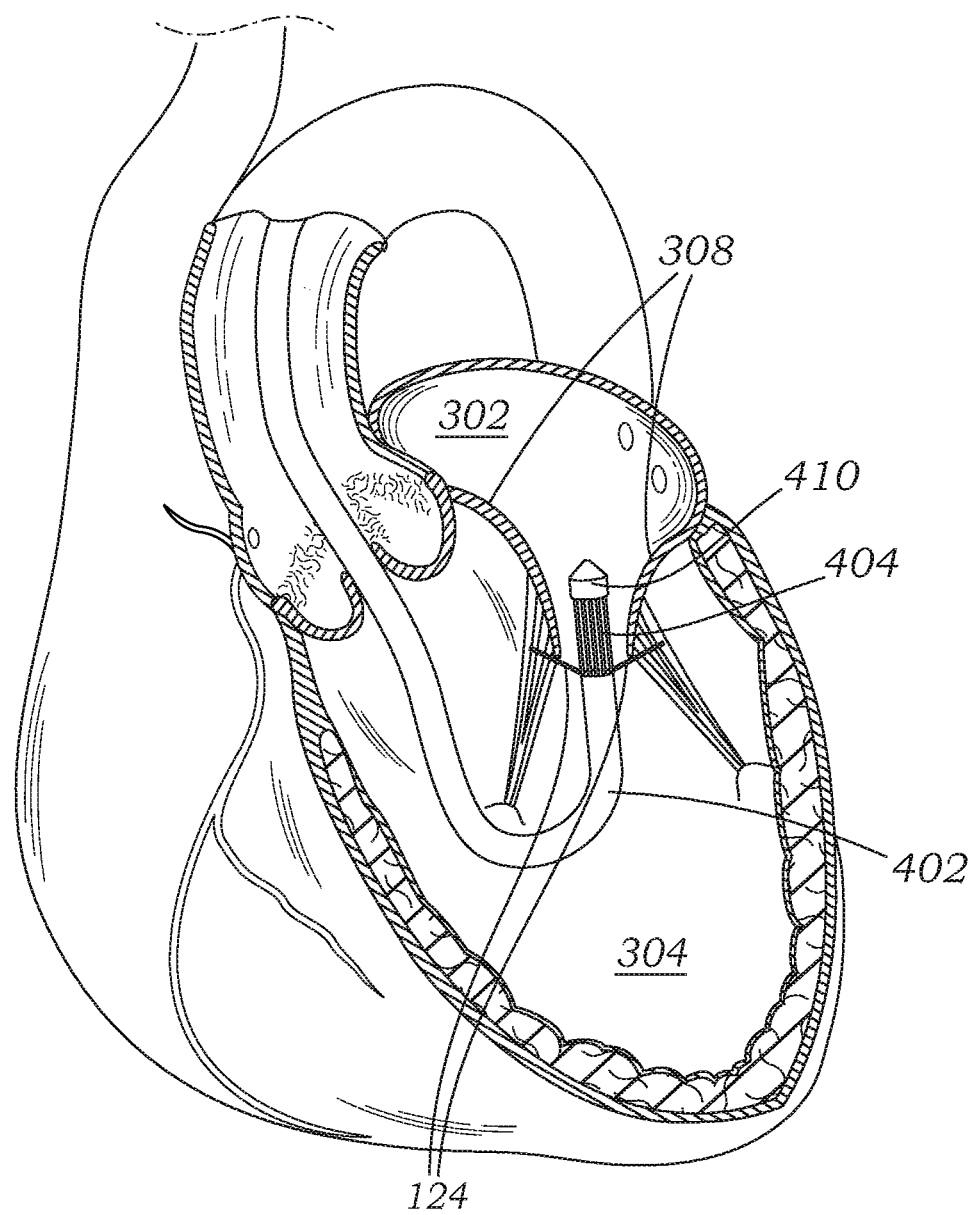
FIG. 19 illustrates a transfemoral delivery approach.

FIGS. 18-21 illustrate delivery approaches by which the delivery system 400 can be used to deliver a prosthetic valve to a patient's native mitral valve. FIGS. 18 and 19 illustrate that delivery from the ventricular side of the native mitral annulus 308 can be accomplished via transventricular and transfemoral approaches, respectively. To deliver a prosthetic valve including frame 100 to a patient's native mitral valve from the ventricular side of the native mitral annulus 308, the prosthetic valve can be loaded into the delivery system 400 so that the atrial end portion 118 of the frame is positioned nearer to the distal end of the delivery system 400 than the ventricular end portion 120 of the frame is. In this embodiment, when the prosthetic valve is delivered to and deployed within the native mitral valve, the atrial end portion 118 is situated within the left atrium 302 and the ventricular end portion 120 is situated within the left ventricle 304.

In some embodiments, a prosthetic valve including protrusions fitted within the distal slots of a slotted sheath such as slotted sheath 404 can be deployed from a delivery system incorporating a retaining element such as retaining element 504, retaining element 510, or retaining element 520, approaching the native mitral valve from the ventricular side of the native mitral valve annulus 308. The prosthetic valve can be compressed to a crimped configuration and loaded into the delivery system such that the protrusions of an atrial flange are retained within the nosecone 410 of the delivery system and the protrusions of a ventricular flange are retained within the outer sheath 402 of the delivery system. The delivery system can then advance the prosthetic valve to the native mitral valve from the ventricular side of the native mitral valve annulus via either a transventricular or a transfemoral approach. In the transventricular approach, the delivery system desirably is inserted through a surgical incision made on the bare spot on the lower anterior ventricle wall.

As shown in FIG. 18, the outer sheath 402 can then be retracted to expose the protrusions 124 of the ventricular flange 106 within the left ventricle 304, and the delivery system can be advanced until the ventricular flange 106 is in contact with the native valve leaflets 306 and adjacent the ventricular side of the native mitral valve annulus 308. The nosecone 410 can then be extended to deploy the protrusions 122 of the atrial flange 104 into the left atrium 302, across the native mitral valve annulus 308 from the protrusions of the ventricular flange 106. In cases where retaining element 504 is used, any tension force applied to the retaining element 504 can be removed, and the retaining element 504 can be actuated (e.g., pulled proximally) so that the retaining element 504 migrates through the holes in the distal extensions 406 of the delivery system until the retaining element 504 is no longer situated within the holes. A pusher shaft 416 of the delivery system can then be extended distally while the slotted sheath 404 is retracted proximally so that the prosthetic valve is deployed from the delivery system and allowed to radially expand within the native mitral valve. In some cases, retaining element 510 or retaining element 520 can be used to help restrain the distal extensions of the slotted sheath 404 against radial expansion during this step. As the prosthetic valve radially expands within the native mitral valve, the spacing between the atrial and ventricular flanges 122, 124, respectively, decreases and they compress the native mitral valve annulus 308. As the prosthetic valve radially expands, the protrusions also angularly expand to their expanded configuration. The delivery system can then be removed from the patient's vasculature, leaving the prosthetic valve in place in the native mitral valve.

Figure 20:
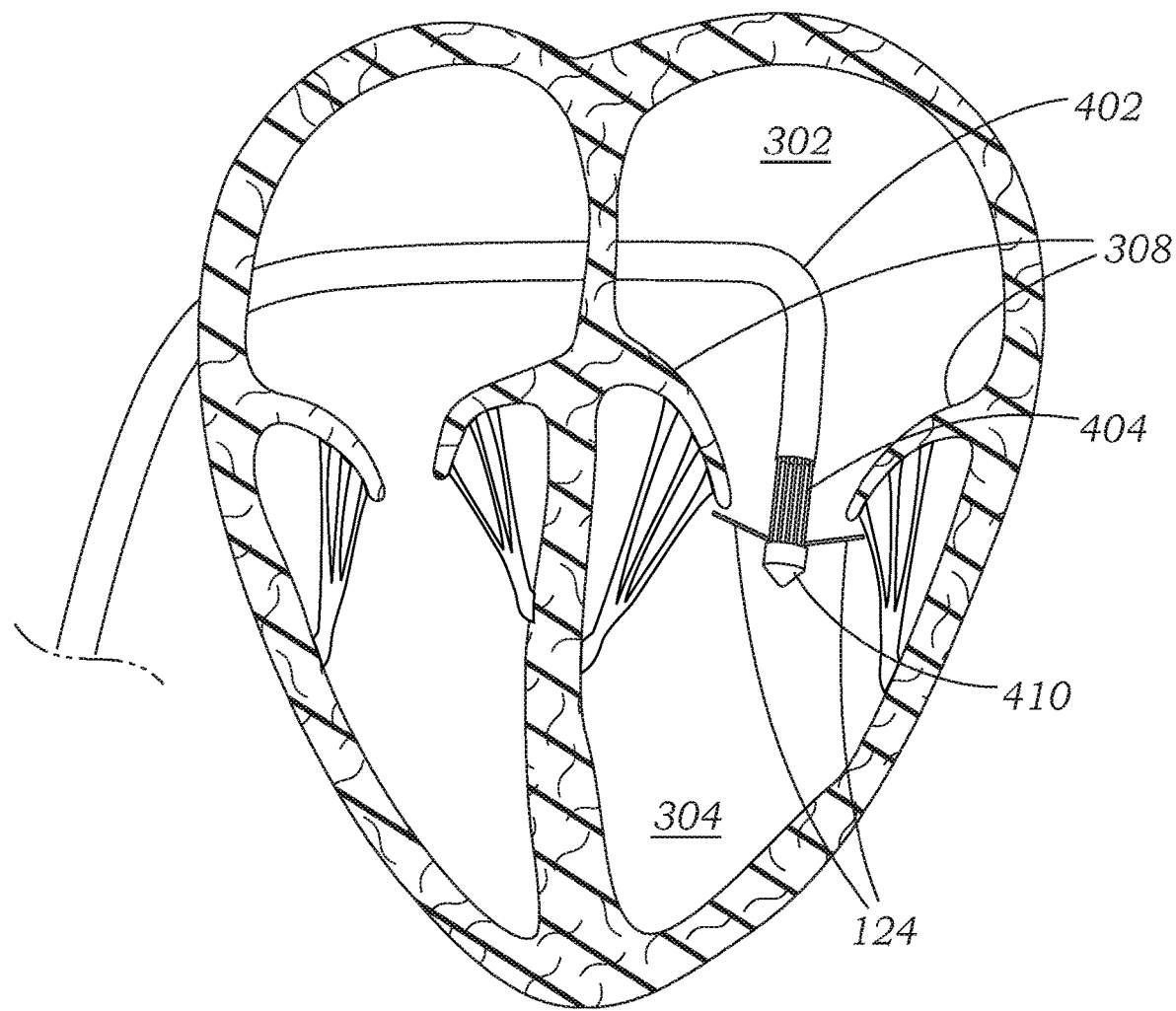
FIG. 20 illustrates a transseptal delivery approach.
Figure 21:
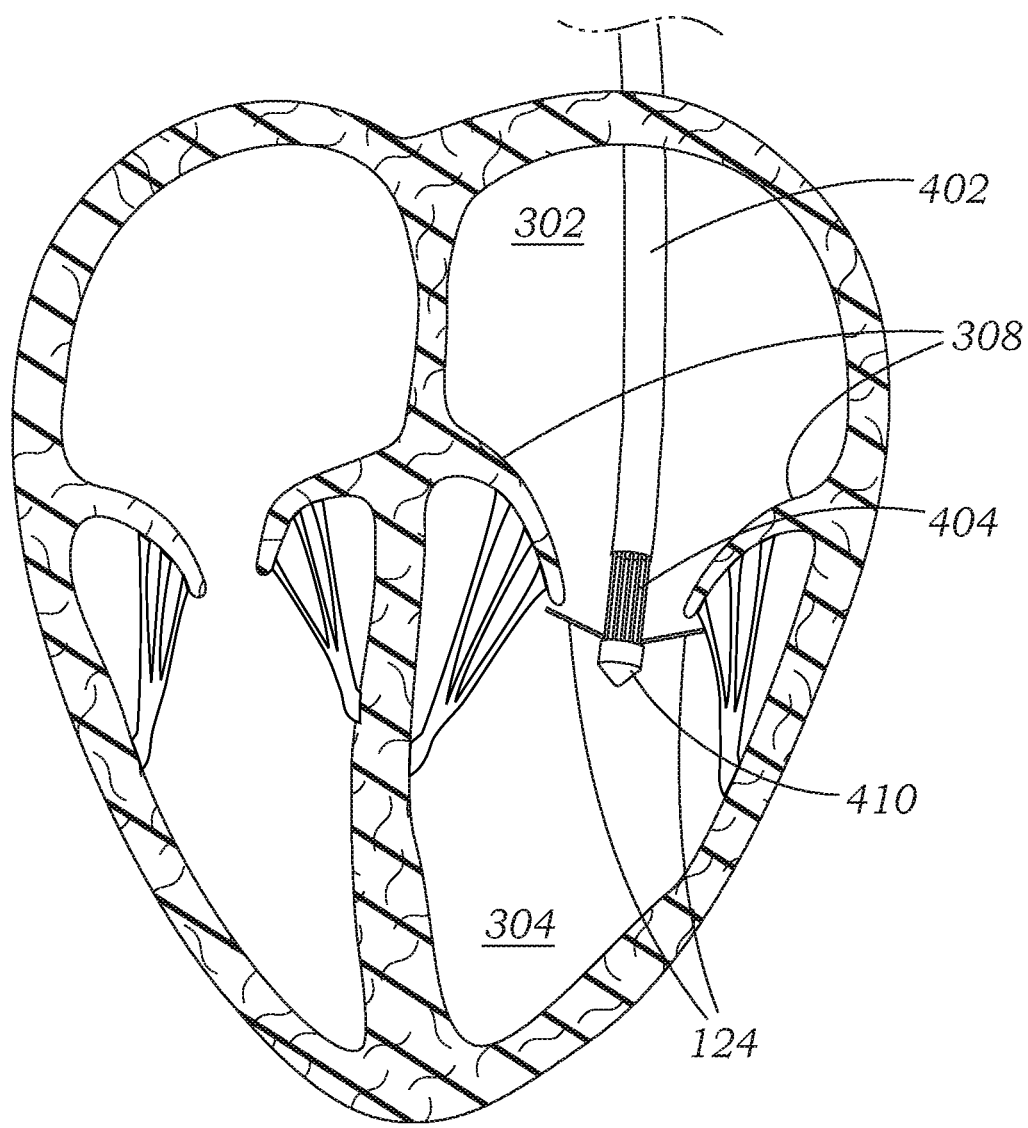
FIG. 21 illustrates a transatrial delivery approach.

FIGS. 20 and 21 illustrate that delivery from the atrial side of the native mitral annulus 308 can be accomplished via transeptal or transatrial approaches. To deliver a prosthetic valve including frame 100 to a patient's native mitral valve from the atrial side of the native mitral annulus 308, the prosthetic valve can be loaded into the delivery system 400 so that the ventricular end portion 120 of the frame is positioned nearer to the distal end of the delivery system 400 than the atrial end portion 118 of the frame is. In this embodiment, when the prosthetic valve is delivered to and deployed within the native mitral valve, the atrial end portion 118 is situated within the left atrium 302 and the ventricular end portion 120 is situated within the left ventricle 304.

In some embodiments, a prosthetic valve including protrusions fitted within the distal slots of a slotted sheath such as slotted sheath 404 can be deployed from a delivery system incorporating a retaining element such as retaining element 504, retaining element 510, or retaining element 520, approaching the native mitral valve from the atrial side of the native mitral valve annulus 308. The prosthetic valve can be compressed to a crimped configuration and loaded into the delivery system such that the protrusions 124 of a ventricular flange 106 are retained within the nosecone 410 of the delivery system and the protrusions 122 of an atrial flange 104 are retained within the outer sheath 402 of the delivery system. The delivery system can then advance the prosthetic valve to the native mitral valve from the atrial side of the native mitral valve annulus via either a transeptal or a transatrial approach.

The nosecone 410 can then be extended to deploy the protrusions 124 of the ventricular flange 106 within the left ventricle 304, and the delivery system can be retracted until the ventricular flange 106 is in contact with the native valve leaflets 306 and adjacent the ventricular side of the native mitral valve annulus 308. The outer sheath 402 can then be retracted to deploy the protrusions 122 of the atrial flange 104 into the left atrium 302, across the native mitral valve annulus 308 from the protrusions of the ventricular flange 106. In cases where retaining element 504 (FIG. 17A) is used, any tensile force applied to the retaining element 504 can be removed, and the retaining element 504 can be actuated so that the retaining element 504 migrates through the holes in the distal extensions 406 of the delivery system until the retaining element 504 is no longer situated within the holes. The outer sheath 402 and slotted sheath 404 can then be retracted while a pusher shaft 416 of the delivery system is held stationary so that the prosthetic valve is exposed from the delivery system and allowed to radially expand within the native mitral valve. In some cases, retaining element 510 or retaining element 520 can be used to help restrain the distal extensions of the slotted sheath 404 against radial expansion during this step. As the prosthetic valve radially expands within the native mitral valve, the spacing between the atrial and ventricular flanges 104, 106 decreases and they compress the native mitral valve annulus 308. As the prosthetic valve radially expands, the protrusions also angularly expand to their expanded configuration. The delivery system can then be removed from the patient's vasculature, leaving the prosthetic valve in place in the native mitral valve.

In embodiments in which protrusions of the frame of a prosthetic valve extend through the distal slots 408 of the slotted sheath 404, the angular compression of the protrusions makes them narrower, and thus easier to navigate to the native mitral valve. For example, the native mitral valve can include chordae tendineae 310 (FIG. 18), which tether the leaflets 306 to the walls of the left ventricle 304. The chordae tendineae 310 can interfere with delivery of a prosthetic valve to the native mitral valve (particularly from the ventricular side of the native mitral annulus 308), and angularly compressing the protrusions can facilitate the navigation of the protrusions through the chordae tendineae 310.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B and C." As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of implanting a prosthetic mitral valve, comprising:

inserting a distal end portion of a delivery apparatus into a patient's body, wherein the prosthetic mitral valve is disposed along the distal end portion of the delivery apparatus in a radially compressed state, the prosthetic mitral valve comprising:

a radially collapsible and expandable annular body defining a central axis and a lumen extending therethrough from an inlet to an outlet of the annular body, the annular body comprising a network of struts interconnected at a plurality of nodes to form a plurality of open cells;

an atrial flange coupled to the annular body and extending radially away from the annular body, the atrial flange comprising a plurality of radially extending atrial protrusions;

a ventricular flange coupled to the annular body and extending radially away from the annular body, the ventricular flange comprising a plurality of radially extending ventricular protrusions;

three angularly spaced, longitudinally extending commissure support posts of fixed length extending in parallel with each other from the ventricular flange toward a ventricular end of the prosthetic valve; and a valve member comprising three leaflets coupled to the commissure support posts;

wherein the atrial protrusions are connected to a first set of nodes of the plurality of nodes and the ventricular protrusions are connected to a second set of nodes of the plurality of nodes, wherein the first set of nodes is axially spaced from the second set of nodes;

wherein the annular body has an annulus portion positioned between the atrial flange and the ventricular flange;

positioning the prosthetic mitral valve within the native mitral valve of the patient's heart; and radially expanding the prosthetic mitral valve such that the atrial protrusions and the ventricular protrusions press against opposing sides of the native mitral valve, thereby retaining the prosthetic mitral valve in place;

wherein, after expansion, the commissure support posts support the leaflets of the valve member below the ventricular flange and within the left ventricle of the heart;

wherein the commissure support posts have upper end portions connected to the annulus portion and positioned between the atrial flange and the ventricular flange, and wherein radially expanding the prosthetic mitral valve causes the annulus portion to be positioned within the native mitral valve annulus;

wherein the commissure support posts have a plurality of openings for stitching the leaflets to the commissure support posts.

2. The method of claim 1, wherein a tip of each of the atrial protrusions points in a direction that is substantially orthogonal to the central axis.

3. The method of claim 1, wherein a tip of each of the ventricular protrusions points in a direction that is substantially orthogonal to the central axis.

4. The method of claim 1, wherein the atrial protrusions are angularly offset from the ventricular protrusions.

5. The method of claim 1, wherein the plurality of open cells includes a first circumferentially extending row of cells defining an inlet end of the annular body and a second circumferentially extending row of cells defining an outlet end of the annular body.

6. The method of claim 5, wherein each of the cells of the first row of cells comprises four struts.

7. The method of claim 1, wherein the atrial flange extends away from the annular body such that an angle between the central axis and the atrial flange is 90° after the prosthetic mitral valve is radially expanded.

8. The method of claim 1, wherein the ventricular flange extends away from the annular body such that an angle between the central axis and the ventricular flange is 90 degrees after the prosthetic mitral valve is radially expanded.

9. The method of claim 1, wherein each of the atrial protrusions and each of the ventricular protrusions comprises a first radial strut coupled to a first node of the annular body and extending radially away from the annular body, a second radial strut coupled to a second node of the annular body and extending radially away from the annular body, a first angled strut coupled at an angle to the first radial strut, and a second angled strut coupled at an angle to the second radial strut and coupled to the first angled strut.

10. The method of claim 1, wherein a distance between the atrial flange and the ventricular flange when the prosthetic valve is in the radially collapsed configuration is between about 4 mm and 30 mm; and
wherein a distance between the atrial flange and the ventricular flange when the prosthetic valve is in the radially expanded configuration is between about 2 mm and about 20 mm.

11. The method of claim 1, wherein the atrial flange extends away from the annular body parallel to the ventricular flange.

12. The method of claim 1, wherein the annular body is cylindrical.

13. A method of replacing the function of a native mitral valve, comprising:
inserting a distal end portion of a delivery apparatus into a patient's body, wherein a prosthetic mitral valve is disposed along the distal end portion of the delivery apparatus in a radially compressed state, the prosthetic mitral valve comprising:
a radially collapsible and expandable annular body defining a central axis and a lumen extending therethrough from an inlet to an outlet of the annular body, the annular body comprising a network of struts interconnected at a plurality of nodes to form a plurality of open cells;
an atrial flange coupled to the annular body and extending radially away from the annular body, the atrial flange comprising a plurality of radially extending atrial protrusions;
a ventricular flange coupled to the annular body and extending radially away from the annular body, the ventricular flange comprising a plurality of radially extending ventricular protrusions connected to the annular body at a plurality of locations;
three angularly spaced, longitudinally extending commissure support posts of fixed length extending in parallel with each other from the ventricular flange toward a ventricular end of the prosthetic valve, wherein the commissure support posts extend substantially the entire length of the annular body; and
a valve member comprising three leaflets coupled to the commissure support posts;
wherein the atrial protrusions are connected to a first set of nodes of the plurality of nodes and the ventricular protrusions are connected to a second set of nodes of the plurality of nodes, wherein the first set of nodes is axially spaced from the second set of nodes;
positioning the prosthetic mitral valve adjacent the native mitral valve of the patient's heart; and
deploying the atrial flange on an atrial side of the native mitral valve; and
deploying the ventricular flange on a ventricular side of the native mitral valve;
wherein, following deployment of the atrial flange and the ventricular flange, the commissure support posts extend below the native mitral valve and the locations at which the ventricular protrusions are connected to the annular body.

14. The method of claim 13, wherein a tip of each of the atrial protrusions points in a direction that is substantially orthogonal to the central axis.

15. The method of claim 13, wherein a tip of each of the ventricular protrusions points in a direction that is substantially orthogonal to the central axis.

16. The method of claim 13, wherein the atrial protrusions are angularly offset from the ventricular protrusions.

17. The method of claim 13, wherein the commissure support posts have upper end portions connected to an annulus portion of the annular body positioned between the atrial flange and the ventricular flange, and wherein radially expanding the prosthetic mitral valve causes the annulus portion to be positioned within the native mitral valve annulus.

18. The method of claim 13, wherein the atrial protrusions and the ventricular protrusions press against the atrial and ventricular sides of the native valve, thereby retaining the prosthetic mitral valve in place.

19. The method of claim 13, wherein the atrial flange extends away from the annular body parallel to the ventricular flange.

\* \* \* \* \*